(12) United States Patent
Jung et al.

(10) Patent No.: US 11,402,904 B1
(45) Date of Patent: *Aug. 2, 2022

(54) SYSTEMS AND METHODS FOR PROVIDING HAPTIC FEEDBACK WHEN INTERACTING WITH VIRTUAL OBJECTS

(71) Applicants: Ranu Jung, Miami, FL (US); Andres E. Pena Serrada, Miami, FL (US)

(72) Inventors: Ranu Jung, Miami, FL (US); Andres E. Pena Serrada, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/455,817

(22) Filed: Nov. 19, 2021

Related U.S. Application Data

(63) Continuation of application No. 17/214,533, filed on Mar. 26, 2021, now Pat. No. 11,199,903.

(51) Int. Cl.
| | |
|---|---|
| *G06F 3/01* | (2006.01) |
| *A61N 1/36* | (2006.01) |
| *A61B 5/00* | (2006.01) |
| *A61N 1/04* | (2006.01) |

(52) U.S. Cl.
CPC .......... *G06F 3/014* (2013.01); *A61B 5/6824* (2013.01); *A61B 5/6825* (2013.01); *A61N 1/0456* (2013.01); *A61N 1/0496* (2013.01); *A61N 1/36034* (2017.08); *G06F 3/015* (2013.01); *G06F 3/016* (2013.01)

(58) Field of Classification Search
CPC .......... G06F 3/014; G06F 3/015; G06F 3/016; A61B 5/6824; A61B 5/6825; A61N 1/0456; A61N 1/0496; A61N 1/36034
See application file for complete search history.

(56) References Cited

U.S. PATENT DOCUMENTS

| | | | | |
|---|---|---|---|---|
| 8,725,265 | B2 * | 5/2014 | Schauer | A61N 1/36003 607/48 |
| 9,229,530 | B1 * | 1/2016 | Wu | G06F 3/016 |
| 9,293,015 | B2 * | 3/2016 | Mar | G06F 3/016 |
| 10,258,271 | B2 * | 4/2019 | Baughman | A61B 5/162 |
| 10,610,099 | B2 * | 4/2020 | Artemiadis | B25J 13/087 |
| 11,198,059 | B2 * | 12/2021 | Konishi | A63F 13/79 |
| 11,199,903 | B1 * | 12/2021 | Jung | A61B 5/6824 |
| 2003/0031993 | A1 * | 2/2003 | Pugh | G09B 23/34 434/262 |
| 2009/0048539 | A1 * | 2/2009 | Lundborg | A61F 2/583 600/595 |
| 2009/0088659 | A1 * | 4/2009 | Graham | G06F 3/016 600/545 |
| 2010/0249637 | A1 * | 9/2010 | Walter | A61H 23/02 601/46 |

(Continued)

*Primary Examiner* — Grant Sitta
(74) *Attorney, Agent, or Firm* — Saliwanchik, Lloyd & Eisenschenk

(57) ABSTRACT

Systems and methods for providing enhanced surface electrical neurostimulation and haptic feedback to a user within a simulation environment are provided. Enhanced surface electrical neurostimulation (eSENS) platforms are able to elicit distally referred tactile percepts while avoiding large charge densities as a method to deliver intuitive haptic feedback during functional tasks.

11 Claims, 13 Drawing Sheets

(56) References Cited

U.S. PATENT DOCUMENTS

| | | | |
|---|---|---|---|
| 2012/0232780 A1* | 9/2012 | Delson | A63F 13/06 |
| | | | 701/400 |
| 2013/0100008 A1* | 4/2013 | Marti | G06F 3/016 |
| | | | 345/156 |
| 2015/0070145 A1* | 3/2015 | Mar | G06F 3/016 |
| | | | 340/407.1 |
| 2015/0306373 A1* | 10/2015 | Bouton | A61N 1/36003 |
| | | | 607/48 |
| 2016/0231814 A1* | 8/2016 | Grant | G06F 3/04842 |
| 2016/0297611 A1* | 10/2016 | Williams | G05D 1/005 |
| 2017/0168773 A1* | 6/2017 | Keller | G06F 3/165 |
| 2017/0294086 A1* | 10/2017 | Kerdemelidis | G08B 6/00 |
| 2018/0140503 A1* | 5/2018 | Kim | A61H 23/02 |
| 2018/0239430 A1* | 8/2018 | Tadi | G06F 3/012 |
| 2019/0212821 A1* | 7/2019 | Keller | G06F 3/0426 |
| 2021/0117002 A1* | 4/2021 | Eagleman | G06F 3/016 |

\* cited by examiner

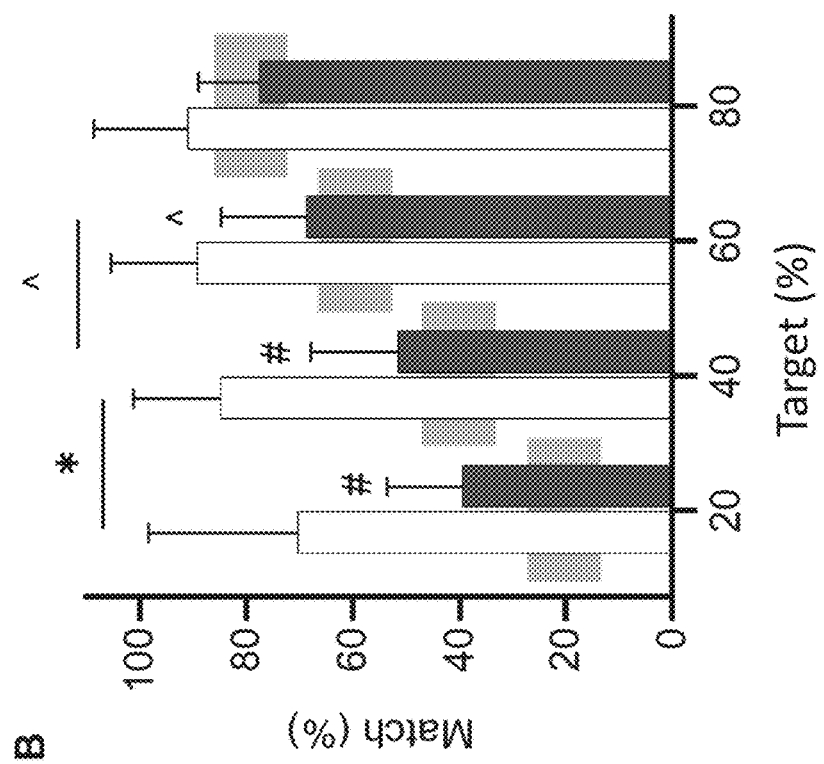
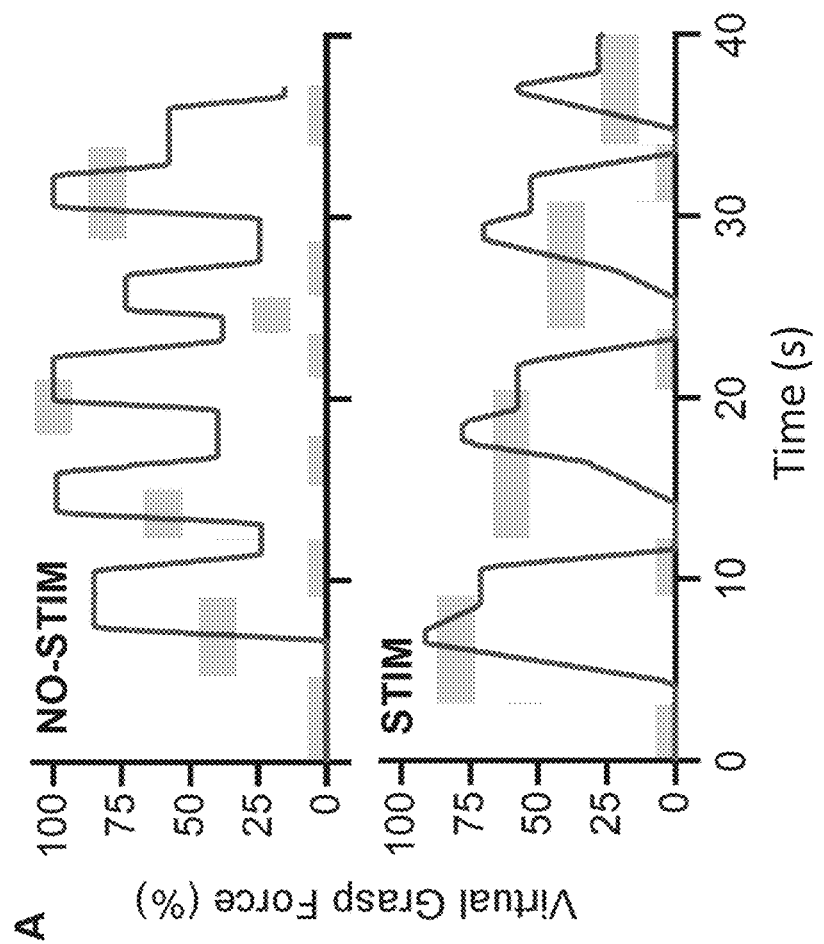
FIG. 6a
FIG. 6b

SYSTEMS AND METHODS FOR PROVIDING HAPTIC FEEDBACK WHEN INTERACTING WITH VIRTUAL OBJECTS

CROSS-REFERENCE TO RELATED APPLICATION

This application is a continuation application of U.S. Ser. No. 17/214,533, filed Mar. 26, 2021, the disclosure of which is hereby incorporated by reference in its entirety, including all figures, tables, and drawings.

BACKGROUND

Sensory feedback is important when exploring and acting on the physical world. As commercially available prosthetic technology is limited by the lack of sensory feedback from the prosthesis, individuals with upper-limb amputation have to rely on visual and sound cues to perform simple control tasks such as grasping an object without crushing it. This results in substantial functional deficits, which impacts quality of life and often leads to prosthesis abandonment. The use of mechanical and electro-tactile sensory substitution has been studied to convey some prosthesis usage information (e.g., grasp force) through an alternate sensory channel by delivering tactile information at specific locations on the user's skin. However, the percept modality and location mismatch of substitution feedback often limits its efficacy and increases the user's cognitive load and response time. Alternatively, electrical stimulation of residual nerves with implantable electrodes has been demonstrated to provide individuals with amputation with intuitive sensory feedback, resulting in functional and psychological benefits. However, the invasive nature of the device implantation procedures is not acceptable to all.

BRIEF SUMMARY

Embodiments of the subject invention provide novel and advantageous systems and methods for providing enhanced surface electrical neurostimulation and haptic feedback to a user within a simulation environment. Enhanced surface electrical neurostimulation (eSENS) 30 platforms of embodiments are able to elicit distally referred tactile percepts while avoiding large charge densities as a method to deliver intuitive haptic feedback during functional tasks. In the context of sensory feedback from prostheses, the evoked tactile information delivered by the eSENS platform according to embodiments of the subject invention could enable individuals with amputation to better control myoelectric prostheses and potentially promote user acceptance of the prosthetic device, notwithstanding that stimulation-induced motor activation or artifact may affect the performance of the myoelectric control system. In addition to the previously mentioned prosthetics applications, the feedback delivered by the eSENS platform according to embodiments of the subject invention may also be used to provide haptic information for many teleoperation applications, and other situations in which the user could benefit from feedback about manipulation and interactions within virtual, augmented, and real environments.

In an embodiment, a system for providing enhanced surface electrical neurostimulation and haptic feedback to a user within a simulation environment can comprise: a neurostimulation subsystem; a contactless real time tracking subsystem; an object properties database; a processor; and a machine-readable medium in operable communication with the processor, the neurostimulation subsystem, the contactless real time tracking subsystem, and the object properties database. The machine-readable medium can have instructions stored thereon that, when executed by the processor, perform the following steps: (1) collecting, from at least one of the neurostimulation subsystem, the contactless real time tracking subsystem, and the object properties database, data can comprise user input data, tracking data, and object properties data; (2) processing the object properties data and the tracking data to create user object interaction information, a tactile contact model, and a neuromorphic mechanoreceptor activation model; (3) processing the user input data and the neuromorphic mechanoreceptor activation model to create an enhanced neurostimulation response signal; and (4) delivering the enhanced neurostimulation response signal to the neurostimulation subsystem, thereby providing the enhanced surface electrical neurostimulation and haptic feedback. The contactless real time tracking subsystem can be configured to track a hand or fingers of the user, and the neurostimulation subsystem may comprise two pairs of self-adhesive hydrogel electrodes placed on a wrist of the user over a median nerve of the user and configured to evoke distally referred tactile percepts in the user when powered in accordance with the enhanced neurostimulation response signal. The tracking data can comprise a non-contact motion capture output can comprise at least one of a one-dimensional (1D) representation, a two-dimensional (2D) representation, and a three-dimensional (3D) representation of at least one of the following: hand position; finger position; finger joint position; finger joint angle; location of any two fingers or visible surfaces of the hand of the user; and distance between any two fingers or visible surfaces of the hand of the user. The step of processing the object properties data and the tracking data to create user object interaction information, a tactile contact model, and a neuromorphic mechanoreceptor activation model further can comprise calculating one or more parameters selected from the group consisting of grip ID, grip aperture, velocity, acceleration, and jerk. The object properties data can comprise at least one of object size data and object hardness data for one or more objects, each object of the one or more objects being a real object or a virtual object. The user input data can comprise at least one of the following values determined using one or more user-in-the-loop (UiTL) calibration routines: a minimum pulse amplitude perceptible to the user; a maximum pulse amplitude creating discomfort in the user; a minimum pulse width detectable to the user; a maximum pulse width creating discomfort in the user; a minimum fusion pulse frequency perceptible to the user; and a maximum saturation pulse frequency perceptible to the user. The neurostimulation response signal can comprise one or more stimulation parameters derived from the user input data to fit the one or more stimulation parameters to an individual user based on user feedback. The one or more stimulation parameters can comprise at least one of a pulse amplitude (PA) of less than 3000 microamps ($\mu A$), a pulse width (PW) of less than 800 microseconds ($\mu s$), and a pulse frequency (PF) of less than 300 Hz. The neurostimulation response signal can comprise one or more current controlled, biphasic, anodic pulse sequences, each sequence having at least one stimulation parameter selected from the group consisting of a PA, a PW, and a PF, the PA being greater than a minimum amplitude of 30 $\mu A$, the PA being less than a maximum amplitude of 3000 $\mu A$, the PW being greater than a minimum width of 100 $\mu s$, the PW being less than a maximum width of 800 $\mu s$, the PF being greater than a fusion frequency of 30 Hz, and the PF being less than a saturation frequency of 300 Hz. The neurostimulation response signal can comprise interleaved sub-threshold current pulses using a channel hopping interleaved pulse scheduling strategy and a bio-inspired charge rate encoding strategy configured to deliver functional stimulation to a proximal nerve and evoke one or more distally referred tactile percepts in the user at a charge density of less than 30 microcoulombs per square centimeter ($\mu C/cm^2$). This charge density is an example only, and the charge density can be, for example, 50% of the value needed to evoke a reliable percept with related art approaches.

In an embodiment, a method for providing enhanced surface electrical neurostimulation and haptic feedback to a user within a simulation environment can comprise: providing a neurostimulation subsystem in operable communication with the user; providing a contactless real time tracking subsystem in operable communication with the user; providing an object properties database; collecting (e.g., by a processor in operable communication with the neurostimulation subsystem, the contactless real time tracking subsystem, and the object properties database), from at least one of the neurostimulation subsystem, the contactless real time tracking subsystem, and the object properties database, data that can comprise user input data, tracking data, and object properties data; processing (e.g., by the processor) the object properties data and the tracking data to create user object interaction information, a tactile contact model, and a neuromorphic mechanoreceptor activation model; processing (e.g., by the processor) the user input data and the neuromorphic mechanoreceptor activation model to create an enhanced neurostimulation response signal; and providing (e.g., by the processor) the enhanced neurostimulation response signal to the neurostimulation subsystem, thereby providing the enhanced surface electrical neurostimulation and haptic feedback. The tracking data can comprise a non-contact motion capture output. The non-contact motion capture output can comprise at least one of a one-dimensional (1D) representation, a two-dimensional (2D) representation, and a three-dimensional (3D) representation of at least one of the following: hand position; finger position; finger joint position; finger joint angle; and locations of, and distance between, any two fingers or visible surfaces of a hand of the user. The step of processing the object properties data and the tracking data to create user object interaction information, a tactile contact model, and a neuromorphic mechanoreceptor activation model further can comprise calculating one or more parameters selected from the group consisting of grip ID, grip aperture, velocity, acceleration, and jerk. The object properties data can comprise at least one of object size data and object hardness data for one or more objects, each object of the one or more objects being a real object or a virtual object. The user input data can comprise at least one of the following values determined using one or more user-in-the-loop (UiTL) calibration routines: a minimum pulse amplitude perceptible to the user; a maximum pulse amplitude creating discomfort in the user; a minimum pulse width detectable to the user; a maximum pulse width creating discomfort in the user; a minimum fusion pulse frequency perceptible to the user; and a maximum saturation pulse frequency perceptible to the user; and the neurostimulation response signal can comprise one or more stimulation parameters derived from the user input data to fit the one or more stimulation parameters to an individual user based on user feedback. The one or more stimulation parameters can comprise a PA of less than 3000 microamps ($\mu A$), a PW of less than 800 microseconds ($\mu s$), and a PF of less than 300 Hz. The neurostimulation response signal can comprise one or more current controlled, biphasic, anodic pulse sequences, each sequence having at least one stimulation parameter selected from the group consisting of a PA, a PW, and a PF, the PA being greater than a minimum amplitude of 30 $\mu A$, the PA being less than a maximum amplitude of 3000 $\mu A$, the PW being greater than a minimum width of 100 $\mu s$, the PW being less than a maximum width of 800 $\mu s$, the PF being greater than a fusion frequency of 30 Hz, and the PF being less than a saturation frequency of 300 Hz. The neurostimulation response signal can comprise interleaved sub-threshold current pulses using a channel hopping interleaved pulse scheduling strategy and a bio-inspired charge rate encoding strategy configured to deliver functional stimulation to a proximal nerve and evoke one or more distally referred tactile percepts in the user at a charge density of less than 30 microcoulombs per square centimeter ($\mu C/cm^2$).

BRIEF DESCRIPTION OF DRAWINGS

FIG. 6a is a chart showing the effect of stimulation, according to an embodiment of the subject invention, on the ability to achieve target levels of virtual grasp force.

FIG. 6b is a chart showing the effect of stimulation, according to an embodiment of the subject invention, on the ability to achieve target levels of virtual grasp force.

DETAILED DESCRIPTION

Figure 1:
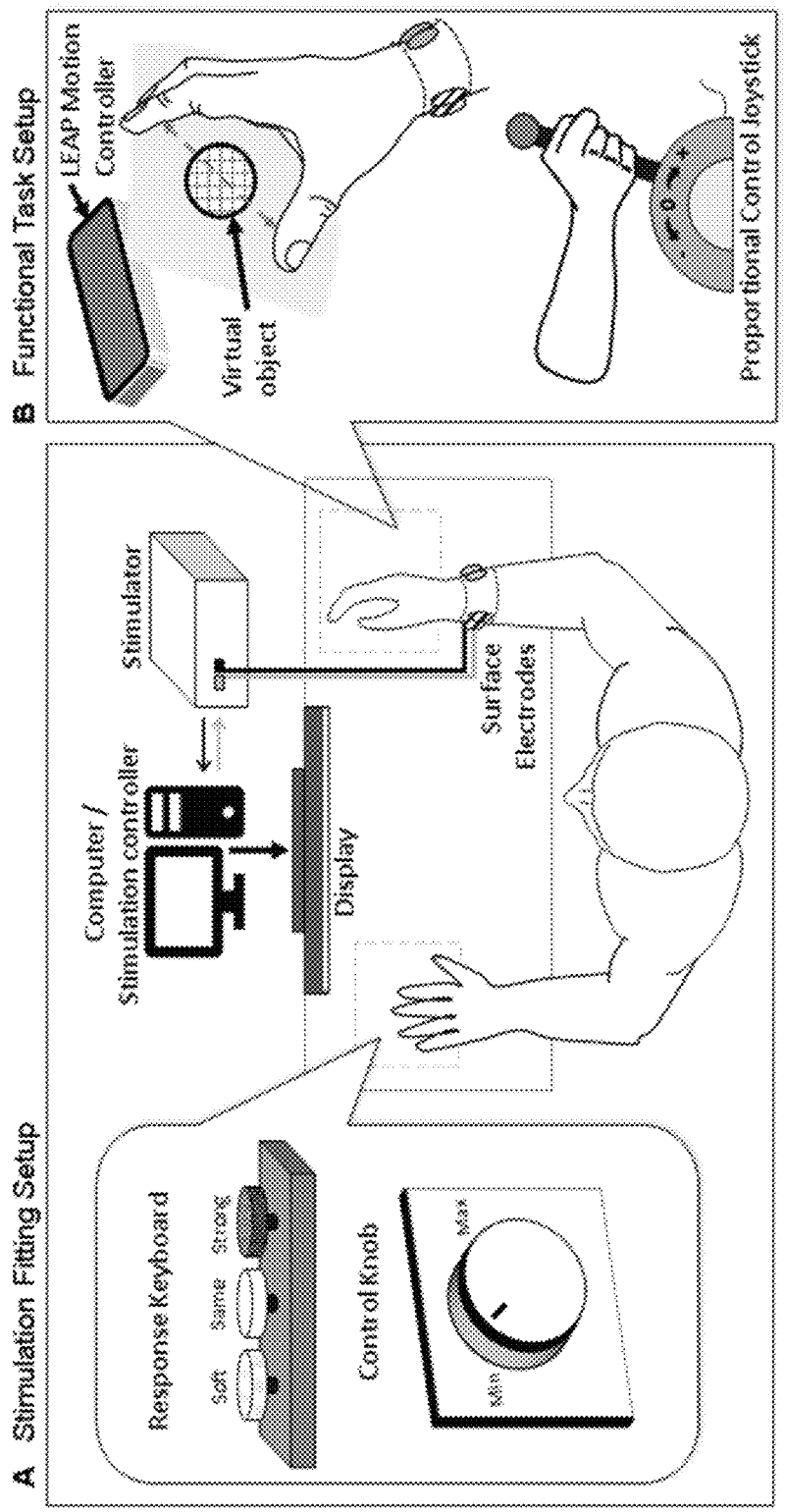
FIG. 1 is a representation of an experimental setup for stimulation fitting (A) and functional tasks (B), according to an embodiment of the subject invention.

Embodiments of the subject invention provide novel and advantageous systems and methods for providing enhanced surface electrical neurostimulation and haptic feedback to a user within a simulation environment. Enhanced surface electrical neurostimulation (eSENS) platforms of embodiments are able to elicit distally referred tactile percepts while avoiding large charge densities as a method to deliver intuitive haptic feedback during functional tasks. In the context of sensory feedback from prostheses, the evoked tactile information delivered by the eSENS platform according to embodiments of the subject invention could enable individuals with amputation to better control myoelectric prostheses and potentially promote user acceptance of the prosthetic device, notwithstanding that stimulation-induced motor activation or artifact may affect the performance of the myoelectric control system. In addition to the previously mentioned prosthetics applications, the feedback delivered by the eSENS platform according to embodiments of the subject invention may also be used to provide haptic information for many teleoperation applications, and other situations in which the user could benefit from feedback about manipulation and interactions within virtual, augmented, and real environments.

Teleoperation of mobile robots has been widely used to perform remote surgical procedures, explore constricted or dangerous environments, transport and dispose dangerous substances, and carry out firefighting and rescue missions. Some military and police applications include advanced unmanned aerial and terrestrial vehicles, and robotics for explosive device disposal, minimizing risk to personnel. Immersive virtual and augmented reality technologies allow users to interact with virtual environments and even other individuals. This expanding field has had a large influence within the gaming industry, has been widely used for development of surgical training protocols, data visualization and manipulation in scientific research, and for expanding the options of social interaction within virtual worlds. A desired feature of teleoperation systems and virtual or augmented reality environments is interaction transparency. This is when users cannot distinguish between operating in a local or real environment, and a distant or virtual environment. A critical component of transparency is the provision of the necessary sensory feedback, including visual, auditory and haptic cues. Teleoperators typically control the remote devices out of direct sight, relying on data from sensors and cameras. This requires a complex combination of the operator's cognitive, perceptual, and motor skills (Lathan and Tracey, 2002). The lack of intuitive feedback from these devices can limit the operator's ability to perform complicated manipulation tasks, especially when trying control to complex components such as a manipulator arm with many degrees of freedom. Traditional mechanical haptic feedback interfaces for teleoperation or virtual interaction purposes are limited by the hardware design. The size and weight of these devices can be restrictive and could have an effect on feedback perception. This problem can be exacerbated when multiple devices are coupled together to increase the amount of haptic information conveyed to the user.

The eSENS platforms according to embodiments of the subject invention have the potential to provide more intuitive haptic feedback without the restrictive design of traditional wearable mechanical feedback systems. The evoked sensations can be used to replicate real-world interaction forces in order to enhance virtual object manipulation tasks and improve operation of remote-controlled devices. Additionally, this feedback can be used to provide information that is not available in the physical world, such as force limit indicators that serve as training cues to enhance force skill learning during precise telesurgery tasks and surgical simulations.

The information delivered by the feedback system according to embodiments of the subject invention may be further enhanced by application of methods within the scope of the subject invention, such as implementing multi-channel stimulation schemes where multiple electrode pairs targeting different nerves or different parts of the same nerve, evoke percepts in different areas of the hand. These enhanced percepts may replicate complex interactions with different types of objects and provide more realistic object manipulation cues that go beyond size and hardness, including object shape, weight and texture, as well as event cues such as object slippage or breakage, thus enabling users to execute virtual or remote manipulation tasks with high precision according to embodiments of the subject invention.

Certain embodiments of the subject invention adopt surface electrical stimulation to deliver task-related sensory feedback, as it is capable of evoking more intuitive somatotopically-matched percepts. However, in contrast with related art systems, a myoelectric prosthetic hand is not utilized to assess closed-loop control performance. Instead, a proportional control joystick can be used to mitigate for potential masking effects of myoelectric limb control expertise in closed-loop control performance. In addition, the hand used to control the joystick was contralateral to the stimulation, as to avoid motion of the stimulated wrist. It is contemplated within certain embodiments of the subject invention to apply closed-loop control with a myoelectric hand, either contralateral or ipsilateral to the stimulation.

During the graded control experiments in this study the direction of target approach was not controlled. That is, during testing of certain embodiments of the subject invention users were allowed to oscillate around the target until they sensed they had reached it using the feedback from the eSENS platform. It is contemplated within certain embodiments of the subject invention to use a single attempt method in which subjects are instructed to approach the target from one direction and stop once they feel they have reached it. It is contemplated within certain embodiments of the subject invention to utilize additional sensory channels (e.g. delivering proprioceptive feedback to the ulnar nerve)

The eSENS platform in accordance with certain embodiments of the subject invention was assessed as a method to deliver intuitive haptic feedback during functional tasks. These functional studies demonstrated that the artificial sensory feedback delivered by the eSENS platform according to certain embodiments of the subject invention may help improve the functionality of prosthetic limbs, enhance teleoperation performance and enable individuals to execute virtual or remote manipulation tasks with high precision without relying solely on visual or auditory cues.

In some embodiments, systems and methods can be provided for providing haptic feedback based on real-time tracking of the user's interactions with objects within a virtual space. A user's hands and fingers are tracked in real-time (e.g. using wireless sensors and/or contactless optical tracking approaches). Custom algorithms parse the hand tracking data and calculate the user's hand position and posture, including for example, hand aperture. The hand tracking data is used to determine whether the user is making contact with an object of known physical properties in a virtual environment, and to generate real-world manipulation cues such as contact locations and forces. For instance, if the hand aperture is equal or less than the virtual object's uncompressed size, the algorithms may estimate physical parameters of the virtual object, the virtual or physical environment and the user, e.g., the amount of object compression and resulting grasping force. This information is then used with known neurophysiological behavior to predict activation of mechanoreceptors in the area of the hand contacting the virtual object. The percept intensity information is then used to control the sensory feedback system to evoke intuitive percepts that represent the virtual interaction cues. As the user "squeezes" a virtual object, the perceived stimulation intensity starts to increase. For instance, squeezing a hard object would ramp up the perceived grasp force much faster than a more compressible, softer object. Depending on the characteristics of the perceived stimulation intensity, users can classify virtual objects according to their perceived physical properties.

In certain embodiments of the subject invention, electrical nerve stimulation (non-invasive or invasive electrical neurostimulation) can be used to evoke intuitive tactile percepts for haptic feedback. When electrical pulses are delivered to different parts of the peripheral nerves that carry sensory information from different sensory endings in the hands, they can evoke distally referred sensations that feel as if they are coming from different areas of the hand. Since the stimulation is delivered proximal to the hand, using electrical nerve stimulation can evoke intuitive distally referred tactile percepts (feeling as if they come from the hand) via peripheral nerves.

Figure 7:
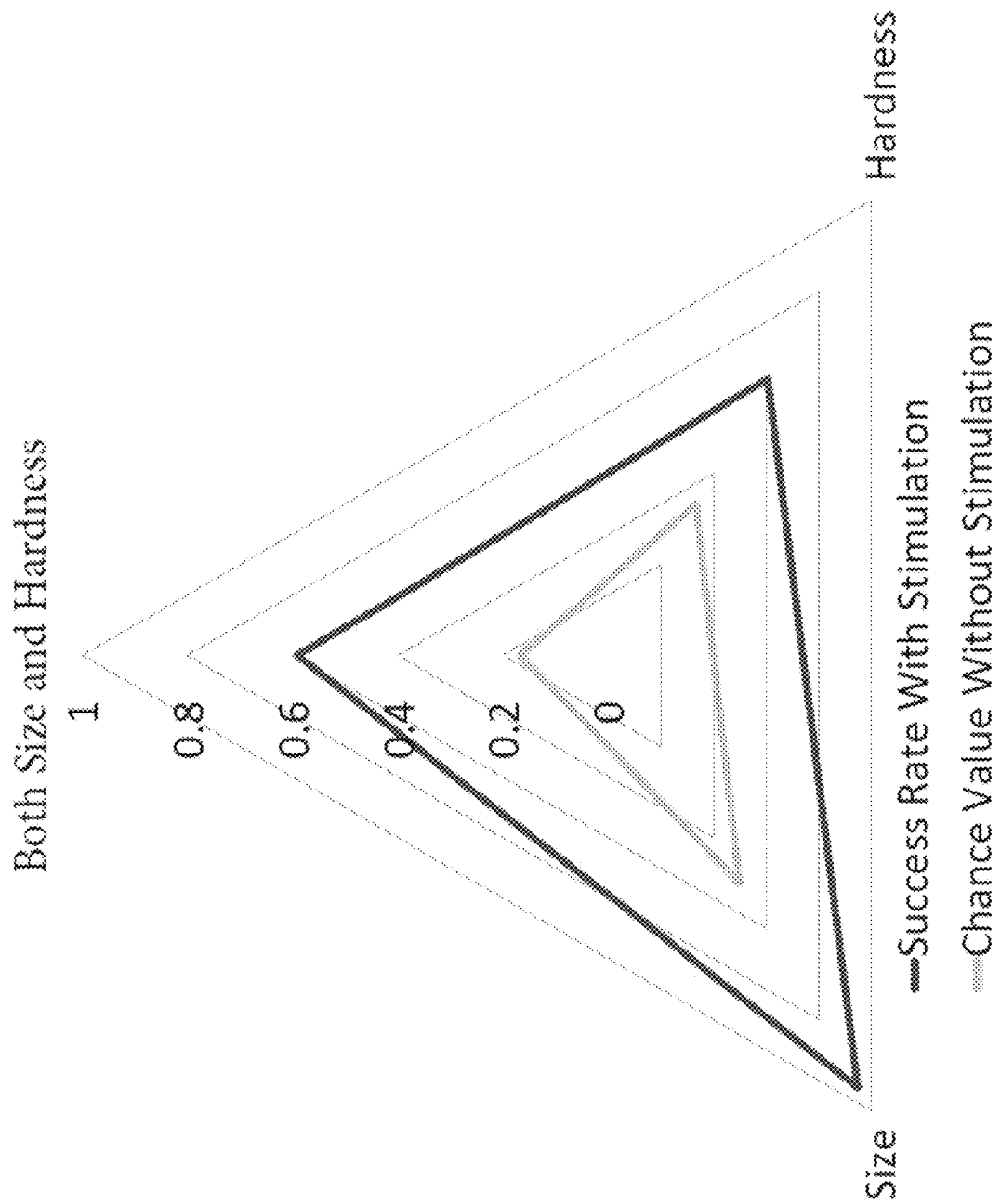
FIG. 7 is a representation of perceived object profile success rate by category with and without stimulation in accordance with an embodiment of the subject invention.

During human subject trials testing certain embodiments of the subject invention, four able-bodied adults were able to integrate percept intensity information delivered by non-invasive neurostimulation as they grasped virtual objects in front of them to successfully determine their size and hardness. During virtual object classification using a system based on certain embodiments of the subject invention, the chance of correctly identifying the object size or hardness alone was 50% and 33.3%, respectively, while the chance of correctly identifying size and hardness together was 16.7%. During an experimental session, each of six virtual object profiles was presented six times, for 36 double-blind presentations. Subjects were able to differentiate between large and small objects much better than chance, with an average success rate (mean±SD) of 98.61±2.77%, $p<0.0001$. Subjects successfully classified virtual objects by their hardness with success rates significantly greater than chance for large objects (70.83±23.70%, $p<0.001$) and small objects (54.17±26.71%, $p=0.019$). All subjects successfully classified both object size and hardness combined, with success rates significantly greater than chance (62.5±17.84%, $p<0.005$). FIG. 7 shows a graphical representation of these results.

When grasping objects, cutaneous mechanoreceptors in the fingers provide relevant information about their characteristics and how much force is being used to grasp them. However, this information is not available during the manipulation of objects in virtual or augmented reality environments. In accordance with embodiments of the subject invention, different stimulation approaches (i.e. electrical or mechanical) could be used to replicate real-world interaction cues to provide complimentary haptic feedback in able-bodied individuals, or as replacement feedback after the loss of sensory function. This could enhance manipulation tasks in teleoperation applications, and other situations in which the user could benefit from feedback about manipulation and interactions within virtual, augmented, and real environments. Additionally, in certain embodiments haptic feedback can be used to provide information that is not available in the physical world, such as force limit indicators that serve as training cues to enhance force skill learning during precise telesurgery tasks and surgical simulations. Different haptic feedback approaches can be used to replicate real-world interaction cues to convey information about the manipulation of virtual objects.

Certain embodiments of the subject invention include systems and methods for providing haptic feedback based on real-time tracking of the user's interactions with objects within a virtual space. During human subject trials, able-bodied adults were able to successfully determine the simulated physical properties of virtual objects based on information delivered by non-invasive neurostimulation according to certain embodiments of the subject invention.

Traditional mechanical haptic feedback interfaces for teleoperation or virtual interaction purposes are limited by the hardware design. The size and weight of some of the tracking and stimulation devices can be restrictive and could have an effect on feedback perception. This problem can be exacerbated when multiple devices are coupled together to track multiple degrees of freedom and increase the amount of haptic information conveyed to the user. In some aspects, the subject invention uses real-time hand position and posture data from contactless tracking approaches (e.g. wireless sensors, optical tracking, image recognition from webcam video) to monitor interactions with objects with known physical properties in a virtual environment. This means that there is no need for external tracking devices at the user's hand restricting motion or affecting feedback perception. This interaction information is then processed and used to drive a haptic feedback system (i.e. electrical, mechanical) based on known sensory activation behavior to elicit intuitive percepts.

In certain embodiments the subject invention, traditional mechanical haptic feedback interfaces can be used for teleoperation or virtual interaction purposes. In cases where size and weight of some of the tracking and stimulation devices can be restrictive and could have an effect on feedback perception, especially where such effects can be exacerbated when multiple devices are coupled together to track multiple degrees of freedom and increase the amount of haptic information conveyed to the user, the subject invention may use real-time hand position and posture data from contactless tracking approaches (e.g. wireless sensors, optical tracking, image recognition from webcam video) to monitor interactions with objects with known physical properties in a virtual environment. In certain embodiments, electrical nerve stimulation can be used to evoke intuitive distally referred tactile percept intensity information delivered by non-invasive neurostimulation Certain embodiments include systems and methods for providing haptic feedback based on real-time tracking of the user's interactions with objects within a virtual space. A user's hands and fingers can be tracked in real-time (e.g. using wireless sensors and/or contactless optical tracking approaches). Custom algorithms parse the hand tracking data and calculate the user's hand position and posture, including hand aperture. The hand tracking data is used to determine whether the user is making contact with an object of known physical properties in a virtual environment, and to determine different manipulation cues such as contact locations and forces. For instance, if the hand aperture is equal or less than the virtual object's uncompressed size, the algorithms estimate the amount of object compression and resulting grasping force. This information is then used with known neurophysiological behavior to predict activation of mechanoreceptors in the area of the hand contacting the virtual object. The percept intensity information is then used to control the sensory feedback system to evoke intuitive percepts that represent the virtual interaction cues. As the user "squeezes" a virtual object, the perceived stimulation intensity starts to increase. For instance, squeezing a hard object would ramp up the perceived grasp force much faster than a more compressible, softer object. Depending on the characteristics of the perceived stimulation intensity, users can classify virtual objects according to their perceived physical properties.

Electrical nerve stimulation (non-invasive or invasive) can be used in certain embodiments of the subject invention to evoke intuitive tactile percepts for haptic feedback. When electrical pulses are delivered to different parts of the peripheral nerves that carry sensory information from different sensory endings in the hands, they can evoke distally referred sensations that feel as if they are coming from different areas of the hand. Since the stimulation is delivered proximal to the hand, using electrical nerve stimulation can evoke intuitive distally referred tactile percepts (e.g., feeling as if the sensations come from the hand). During human subject trials testing certain embodiments of the subject invention, able-bodied adults were able to integrate percept intensity information delivered by non-invasive neurostimulation as they grasped virtual objects in front of them to successfully determine their size and hardness. During virtual object classification, the chance of correctly identifying the object size (one of two possible size classifications) or hardness (one or three different hardness classifications) alone was 50% and 33.3%, respectively, while the chance of correctly identifying size and hardness together (one of six possible combinations of size and hardness) was 16.7%. During an experimental session, each of six virtual object profiles was presented six times, for 36 double-blinded presentations. Subjects were able to differentiate between large and small objects much better than chance, with an average success rate (mean±SD) of 98.61±2.77%, $p<0.0001$. Subjects successfully classified virtual objects by their hardness with success rates significantly greater than chance for large objects (70.83±23.70%, $p<0.001$) and small objects (54.17±26.71%, $p=0.019$). All subjects successfully classified both object size and hardness combined, with success rates significantly greater than chance (62.5±17.84%, $p<0.005$).

FIG. 1 is a representation of an experimental setup for stimulation fitting (A) and functional tasks (B) according to an embodiment of the subject invention. In this experimental setup, (A) a seated subject faces a display, and responds to visual cues using keyboard and control knob while receiving neurostimulation according to certain aspects of the subject invention, and (B) a tracking device (e.g., Leap Motion Controller) monitors motions, actions, objects, and physical parameters including hand aperture while the subject performs a virtual object grasp trial.

A test workstation setup can include: a control knob operable to provide a dial input; a response keyboard having two connectors marked as power in and signal out, respectively; and three buttons marked as soft, same, and strong (or similar labels), respectively, as shown in FIG. 1, Panel A. The test workstation setup may further include: a computer stimulation controller; a stimulator in two-way communication (e.g., having input from and output to the computer simulation controller); a display receiving input from the computer stimulation controller providing visual cues and program information to the subject; a workstation having a first working space, optionally at one hand (e.g., at the subject's left hand) configured for input such as the response keyboard and control knob; and a second working space, optionally at one hand (e.g., at the subject's right hand) configured for functional task operations and feedback including physical objects (e.g., a proportional control joystick) and virtual objects (e.g., a tracking device such as a LEAP motion controller having a field of vision and a range, and configured to detect physical parameters including location, confirmation, size, distance, and orientation of objects including the subject's hand) as shown in FIG. 1, Panel A and FIG. 1, Panel B. In certain embodiments the test workstation may include: one or more stimulation outputs (e.g., four surface electrodes), which may be grouped in two or more groups (e.g., two red and two green surface electrodes); connected to other components of the test workstation (e.g., connected to the stimulator by separate red and green wires); configured for non-invasive and rapid deployment to the subject (e.g. aligned for placement at the subject's wrist in a wristband or strap); and grouped for functional alignment with physiological landmarks of the subject (e.g., four surface electrodes in two pairs as indicated by red and green colors, respectively, aligned for placement at specific points above and below the wrist of the subject); as shown in FIG. 1, Panel A and FIG. 1, Panel B. In FIG. 1, Panel B is indicated to be a detail of the second working space, near the right hand of the subject.

Figure 2:
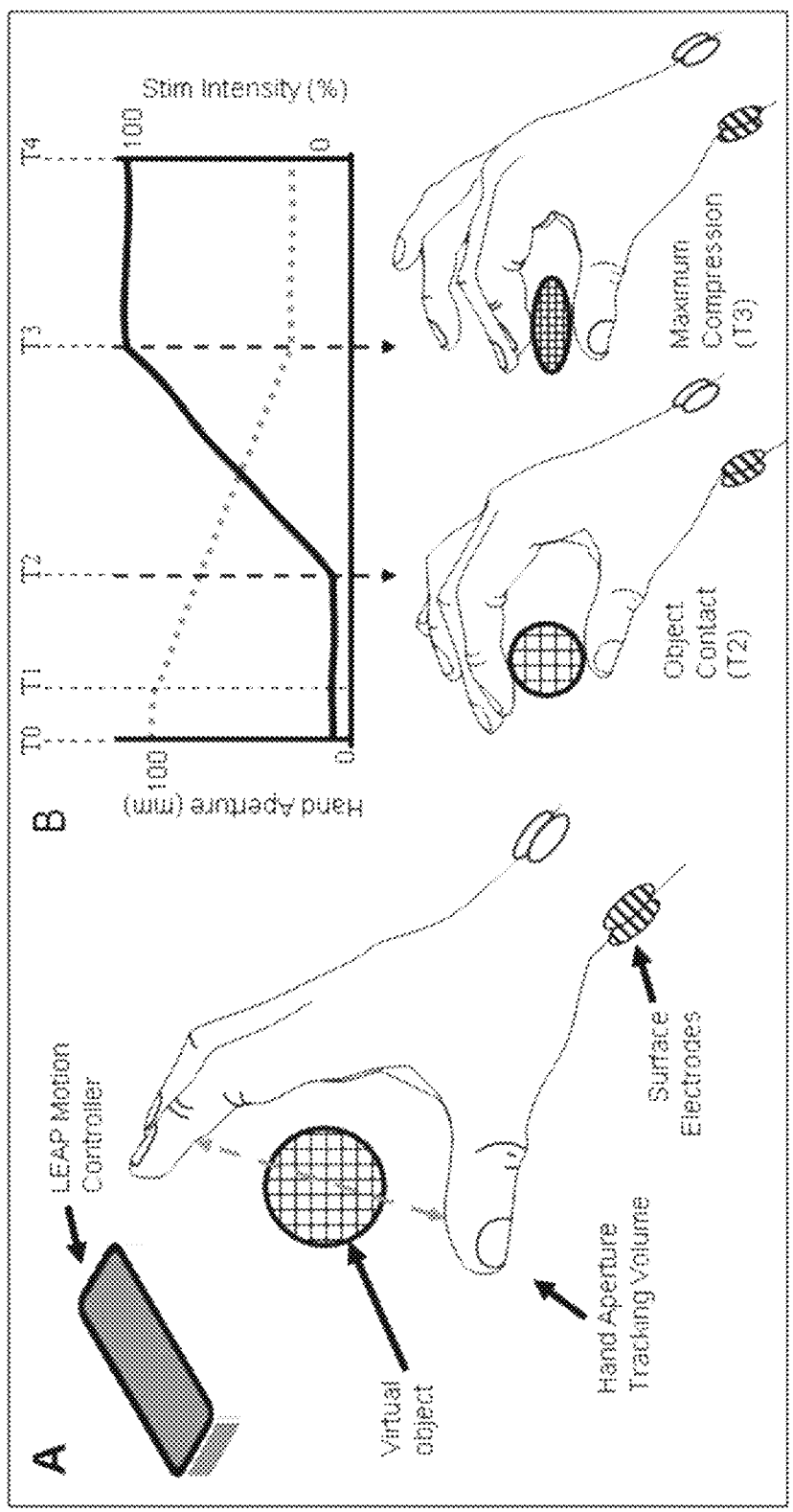
FIG. 2 is a representation of hand aperture tracking during virtual object classification tasks, according to an embodiment of the subject invention.

FIG. 2 is a representation of hand aperture tracking during virtual object classification tasks according to an embodiment of the subject invention. This schematic representation of the system relating changes in hand aperture to percept intensity on electrical stimulation shows in FIG. 2, Panel (A) a tracking device (e.g., A Leap Motion Controller) configured with a field of vision or working range (shown as a shaded area including a part of the subject's body (e.g., the subject's hand) and a virtual object) to measure the subject's hand aperture distance (e.g., the linear distance between the thumb pad and the average horizontal position of the index middle and ring finger pads) as denoted by the dashed line, or to measure the location of and distance between any two fingers or visible surfaces of the hand; and in FIG. 2, Panel (B) the hand aperture data (beginning as the top, dotted trace) was used to determine object contact (as shown in the bottom left representation of the subject's hand in FIG. 2, Panel B) and compression (as shown in the bottom right representation of the subject's hand in FIG. 2, Panel B), and to estimate the resulting grasping force, correlated to a stimulation intensity percentage (beginning as the bottom, solid trace). The full compressive range of the virtual object (shaded region of the chart in the upper half of FIG. 2, Panel B) was linearly mapped to the full range of percept intensities.

The chart in FIG. 2, Panel B shows hand aperture in mm on the left vertical axis, ranging from 0 mm to 100 mm and stim intensity in percentage ranging from 0% to 100% on the right vertical axis. The horizontal axis represents time with a steady state condition from T0 to T1, an object contact feedback horizontal threshold at T2 (marked by a first dashed vertical arrow pointing to a representation of a subject hand aperture in contact with a virtual object), an object maximum compression feedback threshold at T3 (marked by a second dashed vertical arrow pointing to a representation of a subject hand aperture at maximum compression of a virtual object), and a full compression steady state by the end of the charted period at T4.

Looking further at the chart in FIG. 2, Panel B, the dashed line representing the hand aperture data series begins with a flat region indicating initial object contact from T0 to T1, continues through a linear reduction in hand aperture from T1 to T3, and ends with a second flat region indicating minimal hand aperture for this data series from T3 to T4. At T2 the hand aperture data series crosses an upper hand aperture threshold denoting the upper boundary of a horizontal shaded region. At T3 the hand aperture data series aligns with a lower hand aperture threshold denoting the lower boundary of a horizontal shaded region. The solid line representing the stimulation intensity data series begins with a flat region representing minimal stimulation intensity (e.g., a value above zero but less than 10%, alternatively a value of 0%) from T0 to T2, continues through a linear increase in stimulation intensity from T2 to T3, and ends with a second flat region indicating maximum stimulation intensity (e.g., 100% stimulation intensity) from T3 to T4.

Figure 3:
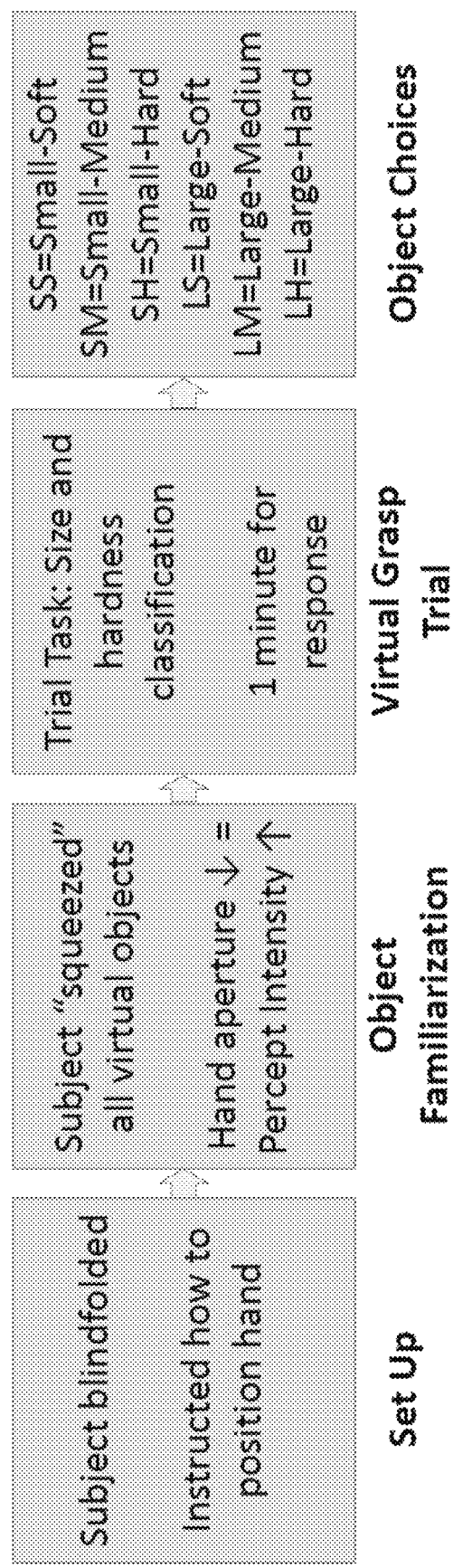
FIG. 3 is a flow chart representing an experimental protocol useful in measuring the effectiveness of certain embodiments of the subject invention.

FIG. 3 is a flow chart representing an experimental protocol useful in measuring the effectiveness of certain embodiments of the subject invention. Beginning at the left edge of FIG. 3 and moving left to right, a set up block includes subject blindfolded and instructed how to position hand. An arrow points from the set up block to an object familiarization block including subject "squeezed" all virtual objects, hand aperture ↓=("down arrow" and "equals sign"), and percept intensity ↑ ("up arrow"). An arrow points from the object familiarization block to a virtual grasp trial block including trial task: size and hardness classification and 1 minute for response. An arrow points from the virtual grasp trial block to an object choices block on the right hand edge of FIG. 3, including SS=small-soft, SM=small-medium, SH=small-hard, LS=large-soft, LM=large-medium, and LH=large-hard.

Figure 4A:
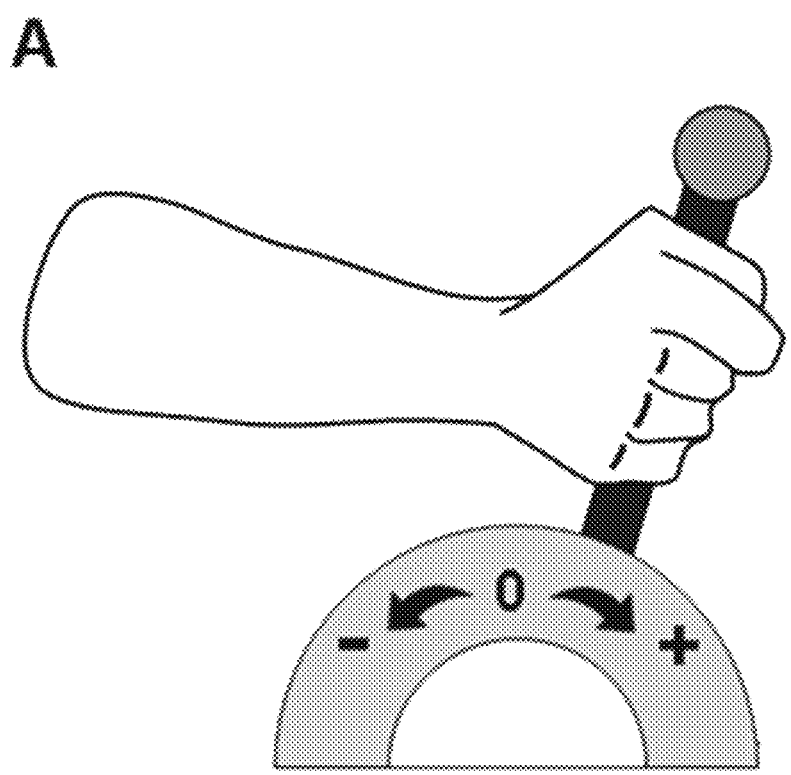
FIG. 4a is a representation of control of virtual grasp force levels during graded control tasks, according to an embodiment of the subject invention.

FIG. 4a is a representation of control of virtual grasp force levels during graded control tasks according to an embodiment of the subject invention, including a representation of a subject hand manipulating joystick with left and right arrows indicating motion of the joystick from a vertical dashed line marked as 0 ("zero") to a forward or right leaning position indicated by a right-leaning dashed line marked with + ("positive"). Also shown is a corresponding rearward or left-leaning dashed line marked with − ("negative"), the base of the joystick and a portion of wire exiting the base of the joystick. In certain embodiments of the subject invention the proportional control joystick may be used by the subject to increase (+) or decrease (−) virtual grasp force levels. The rate of change of force was proportional to the degree of deflection of the joystick.

Figure 4B:
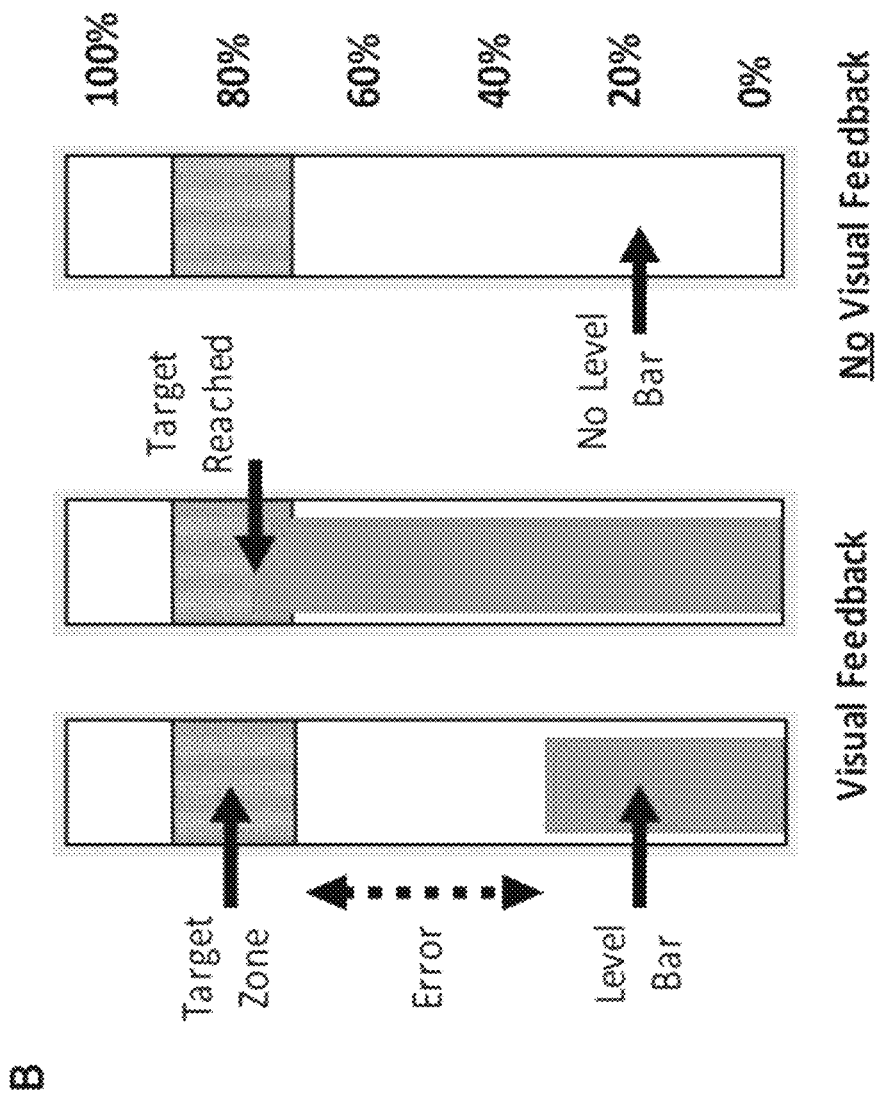
FIG. 4b is a representation of a visual feedback method for control of virtual grasp force levels during graded control tasks, according to an embodiment of the subject invention.

FIG. 4b is a representation of a visual feedback method for control of virtual grasp force levels during graded control tasks according to an embodiment of the subject invention including three representations of a virtual thermometer display device each marked with target zone at 80%±7%. A scale to the right of the rightmost thermometer device shows a common range from 0% at the bottom to 100% at the top of each thermometer. From left to right in FIG. 4b, a first thermometer displays a level bar beginning at 0% and reaching up to 30% and a dashed double-arrow line labelled as error between the top of the level bar and the bottom of the target zone. A second (middle) thermometer shows a level bar within the target zone (at 80%±7%) labelled as target reached. A third thermometer shows only the target zone with the area below labelled as no level bar. The first and second thermometers are commonly labelled as visual feedback, while the third thermometer is labelled as no visual feedback.

In certain embodiments of the subject invention, a computer display may include a representation of a virtual thermometer device with or without a moving level bar which provides visual feedback and one or more target zones (e.g., a ±7% target zone) centered at one or more different target levels (e.g., 6 different target levels including one target level between 70% and 90%).

Figure 5A:
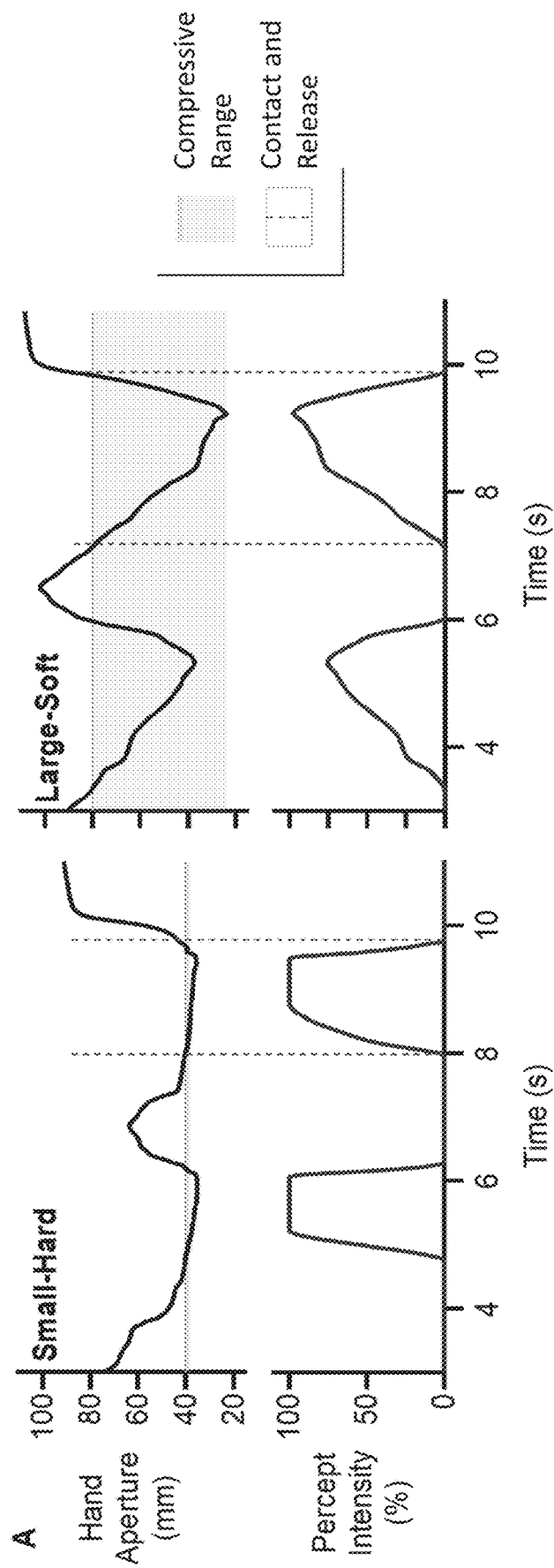
FIG. 5a is a representation of how feedback of grasp force profiles enables identification of virtual object size and hardness in able-bodied subjects, according to an embodiment of the subject invention.

FIG. 5a is a representation of how feedback of grasp force profiles enables identification of virtual object size and hardness in able-bodied subjects according to an embodiment of the subject invention.

The two charts in FIG. 5a show examples of hand aperture (upper) and virtual grasp force profile (lower) traces generated in accordance with an embodiment of the subject invention and recorded from one subject when grasping a small, hard object (left) and a large, soft object (right). Each chart shows two grip and release cycles for each object (small, hard object (left) and a large, soft object (right)), respectively. Each grip cycle on each chart begins with the hand aperture above the compressive range and ends after the hand aperture has returned back above the compressive range. (Both charts are on a horizontal axis showing time in seconds from 0 to 12, with markings at 4, 6, 8, and 10 seconds. Each chart has an upper hand aperture (mm) data series on an upper vertical axis from 20 mm to 100 mm with markings at 20, 40, 60, 80, and 100 mm; and a lower percept intensity (%) data series on a lower vertical axis from 0% to 100% with markings at 0%, 50%, and 100%. The left most chart is labeled as small-hard, and the right most chart is labeled as large-soft. The shaded region in each chart highlights each respective object's compressive range, appearing as a narrow horizontal region centered at about 40 mm on the small-hard chart and as a horizontal range from 20 mm to 80 mm on the large-soft chart; and a pair of dashed vertical lines on each chart represent the object contact and release times for the second gripping of each object, respectively, as shown in a common chart legend.

The small-hard chart shows a hand aperture starting the first grip cycle at 70 mm and getting smaller until crossing into and below the compressive range at 5 seconds, remaining below the compressive range until 6 seconds, crossing into and back above the compressive range at 6 seconds, ending the first grip cycle and with a peak of 60 mm at 7 seconds, remaining above the compressive range until 8 seconds, crossing into and below the compressive range again at 8 seconds, but with a lower slope and more gradual crossing in the second grip cycle, remaining below the compressive range until 10 seconds, crossing into and back above the compressive range at 10 seconds, and remaining above the compressive range until the chart ends at 12 seconds.

The small-hard chart also shows a percept intensity curve in response to the hand aperture according to certain embodiments of the present invention. The response begins and stays at 0% as the first grip cycle begins until at 5 seconds (when the hand aperture enters the compressive range), ramps up quickly to 100% (as the hand aperture crosses through and then below the compressive range), remains at 100% until at 6 seconds (while the hand aperture is below the compressive range), ramps quickly back down to 0% (as the hand aperture crosses through and then above the compressive range), and remains at 0% as the first grip cycle ends and the second grip cycle begins.

The small-hard percept intensity response again begins and stays at 0% as the second grip cycle begins until at 8 seconds (when the hand aperture enters the compressive range), ramps up slightly less quickly in the second grip cycle as compared to the first grip cycle to 100% (as the hand aperture crosses through and then below the compressive range on the second grip cycle with a smaller, flatter slope), remains at 100% until just before 10 seconds (while the hand aperture is below the compressive range), ramps quickly back down to 0% (as the hand aperture crosses through and then above the compressive range), and remains at 0% as the second grip cycle ends.

The large-soft chart shows a hand aperture starting the first grip cycle at 90 mm and getting smaller until crossing into the compressive range at 1 second, decreasing (while remaining within the compressive range) to a minimum of 40 mm at 5 seconds, then increasing (while remaining within the compressive range) until 6 seconds, crossing back above the compressive range at 6 seconds, ending the first grip cycle and with a peak of 100 mm at 6.5 seconds, remaining above the compressive range until 7 seconds, crossing back into the compressive range again at 7 seconds, with a similar slope and reduction in the second grip cycle, decreasing (while remaining within the compressive range) to a minimum of 30 mm at 9 seconds, then increasing (while remaining within the compressive range) until 10 seconds, crossing back above the compressive range at 10 seconds, and remaining above the compressive range until the chart ends at 12 seconds.

The large-soft chart also shows a percept intensity curve in response to the hand aperture according to certain embodiments of the present invention. The response begins and stays at 0% as the first grip cycle begins until at 1 second (when the hand aperture enters the compressive range), ramps up moderately to a peak of around 75% (as the hand aperture reduces within the compressive range), ramps quickly back down to 0% at 6 seconds (as the hand aperture increases within the compressive range then rises above the compressive range), and remains at 0% as the first grip cycle ends and the second grip cycle begins.

The response again begins and stays at 0% as the second grip cycle begins until at 7 seconds (when the hand aperture enters the compressive range), ramps up moderately to a peak of near 100% (as the hand aperture reduces within the compressive range), ramps quickly back down to 0% at 10 seconds (as the hand aperture increases within the compressive range then rises above the compressive range), and remains at 0% as the second grip cycle ends.

Figures 5B, 5C:
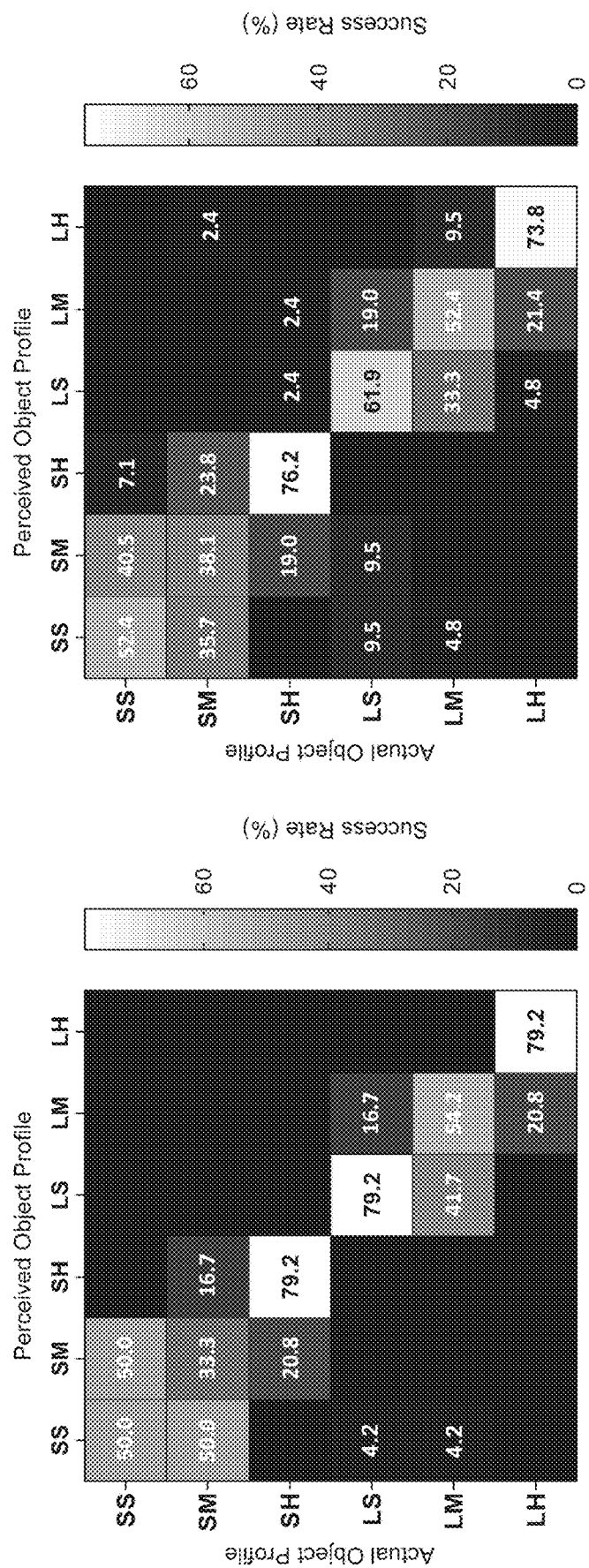
FIG. 5b is a table representing confusion matrices quantifying the perceived size and hardness pairs (left-right), in relation with the ground truth of the actual object profile (up-down). The data was generated using a system and methods according to an embodiment of the subject invention.
FIG. 5c is a table representing confusion matrices quantifying the perceived size and hardness pairs (left-right), in relation with the ground truth of the actual object profile (up-down). The data was generated using a system and methods according to an embodiment of the subject invention.

FIG. 5b is a table representing confusion matrices quantifying the perceived size and hardness pairs (left-right, perceived object profile (%)), in relation with the ground truth of the actual object profile (up-down, actual object profile (%)). The data was generated using a system and methods embodying certain aspects of the subject invention. The average success rate was calculated across all subjects based on 6 virtual object profiles presented to each subject 6 times, for a total of 36 object presentations. SS=Small-Soft; SM=Small-Medium; SH=Small-Hard; LS=Large-Soft; LM=Large-Medium; LH=Large-Hard. Each square of the 36 in the table is color coded to indicate success rate from black for success between 0% and 10% to white for success rate between 70% and 80%. The tabulated data is shown in Table 1.

FIG. 5c is a table representing confusion matrices quantifying the perceived size and hardness combined (left-right), in relation to the actual object profile (up-down). Each block indicates the percentage of responses that were given when all subjects were presented a profile (actual) and classified it (perceived). A diagonal (top left to bottom right) of white blocks with 100% would indicate all responses were correct. Solid black blocks had 0% responses from all the subjects. Random chance would predict a value of 16.7% in every block of the table. The data was generated using a system and methods embodying certain aspects of the subject invention. The average success rate was calculated across all subjects based on 6 virtual object profiles presented to each subject 6 times, for a total of 36 object presentations. SS=Small-Soft; SM=Small-Medium; SH=Small-Hard; LS=Large-Soft; LM=Large-Medium; LH=Large-Hard. Each square of the 36 in the table is color coded to indicate success rate from black for success between 0% and 10% to white for success rate between 70% and 80%. The tabulated data shown in Table 2. FIG. 5b shows results from four subjects (2M,2F), and the results shown in FIG. 5c are from seven subjects (4M, 3F), which includes three new subjects added to the first four subjects from FIG. 5b.

TABLE 1

Agreement (%) between Actual Object Profile and Perceived Object Profile for combined size-hardness pairs in FIG. 5b.

| Agreement (%) | | Perceived Object Profile | | | | | |
|---|---|---|---|---|---|---|---|
| Actual | | SS | SM | SH | LS | LM | LH |
| Object | SS | 50.0 | 50.0 | 0 | 0 | 0 | 0 |
| Profile | SM | 50.0 | 33.3 | 16.7 | 0 | 0 | 0 |
| | SH | 0 | 20.8 | 79.2 | 0 | 0 | 0 |
| | LS | 4.2 | 0 | 0 | 79.2 | 16.7 | 0 |
| | LM | 4.2 | 0 | 0 | 41.7 | 54.2 | 0 |
| | LH | 0 | 0 | 0 | 0 | 20.8 | 79.2 |

FIG. 6a is a chart showing the effect of stimulation according to certain aspects of the subject invention on the ability to achieve target levels of virtual grasp force. Stimulation in accordance with certain embodiments of the subject invention has been shown to improve the ability of a subject to achieve target levels of virtual grasp force. FIG. 6a shows examples of graded control trials showing how one subject attempted to match a series of target levels during the NO-STIM (top) and STIM (bottom) feedback conditions according to one embodiment of the subject invention. The solid trace in each of the top and bottom charts indicates the match level over time without (top) and with (bottom) stimulation, respectively. The shaded boxes indicate the target zone sequences for those specific trials. The shaded target zone values in FIG. 6a are indicated for NO-STIM in Table 3 and STIM in Table 4. The time scale is the same in the top and bottom (STIM vs NO-STIM) charts shown in FIG. 6a.

TABLE 2

Agreement (%) between Actual Object Profile and Perceived Object Profile for combined size-hardness pairs in FIG. 5c.

| Agreement (%) | | Perceived Object Profile | | | | | |
|---|---|---|---|---|---|---|---|
| | | SS | SM | SH | LS | LM | LH |
| Actual Object Profile | SS | 52.4 | 40.5 | 7.1 | 0 | 0 | 0 |
| | SM | 35.7 | 38.1 | 23.8 | 0 | 0 | 2.4 |
| | SH | 0 | 19 | 76.2 | 2.4 | 2.4 | 0 |
| | LS | 9.5 | 9.5 | 0 | 61.9 | 19 | 0 |
| | LM | 4.8 | 0 | 0 | 33.3 | 52.4 | 9.5 |
| | LH | 0 | 0 | 0 | 4.8 | 21.4 | 73.8 |

FIG. 6b is a chart showing the effect of stimulation according to certain aspects of the subject invention on the ability to achieve target levels of virtual grasp force. Match level (mean±SD) was significantly lower with STIM (solid filled bars on the right) than NO-STIM (unfilled empty bars on the left) for target levels of 20%, 40% and 60%; and significantly different between adjacent target levels 40% and 60% with STIM and between adjacent target levels 20% and 40% with NO-STIM. Shaded background boxes indicate the target zone for each target level. Comparisons in this chart used two-way repeated measures ANOVA with Bonferroni multiple pairwise post-hoc comparisons (*$p<0.05$, ˆ$p<0.01$, #$p<0.001$). The shaded target zone values in FIG. 6b are indicated in Table 5.

TABLE 3

Time (s) and Virtual Grasp Force data for NO-STIM Target Zones in FIG. 6a.

| NO-STIM Target zone | Time (s) | Virtual Grasp Force (%) |
|---|---|---|
| 1 | 0-5 | 0-10 |
| 2 | 5-9 | 30-50 |
| 3 | 9-12 | 0-10 |
| 4 | 12-15 | 50-70 |
| 5 | 15-17 | 0-10 |
| 6 | 17-21 | 90-100 |
| 7 | 21-23 | 0-10 |
| 8 | 23-26 | 15-25 |
| 9 | 26-29 | 0-10 |
| 10 | 29-34 | 70-80 |
| 11 | 34-38 | 0-10 |

TABLE 4

Time (s) and Virtual Grasp Force data for STIM Target Zones in FIG. 6a.

| STIM Target zone | Time (s) | Virtual Grasp Force (%) |
|---|---|---|
| 1 | 0-3 | 0-10 |
| 2 | 3-9 | 75-85 |
| 3 | 9-12 | 0-10 |
| 4 | 12-20 | 55-70 |
| 5 | 20-23 | 0-10 |
| 6 | 23-31 | 30-45 |
| 7 | 31-34 | 0-10 |
| 8 | 34-40 | 15-25 |

Figure 6C:
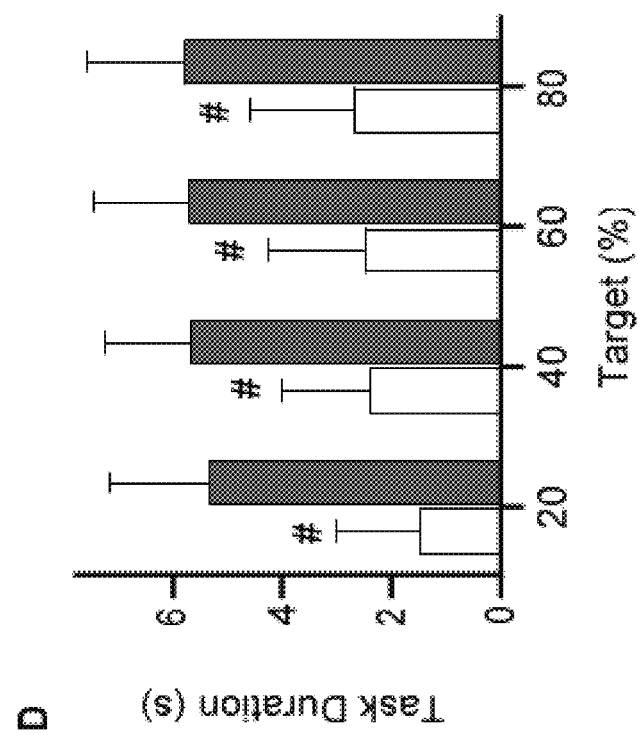
FIG. 6c is a chart showing the effect of stimulation, according to an embodiment of the subject invention, on the ability to achieve target levels of virtual grasp force.

FIG. 6c is a chart showing the effect of stimulation according to certain aspects of the subject invention on the ability to achieve target levels of virtual grasp force. Error (mean±SD) was significantly lower with STIM (solid filled bars on the right) than NO-STIM (unfilled empty bars on the left) for target levels of 20%, 40% and 60%. Comparisons in this chart used two-way repeated measures ANOVA with Bonferroni multiple pairwise post-hoc comparisons (*$p<0.05$, ˆ$p<0.01$, #$p<0.001$).

TABLE 5

Target Zones for Match (%) vs. Target (%) in FIG. 6b.

| | Target (%) | Match (%) |
|---|---|---|
| 1 | 5-37 | 15-25 |
| 2 | 37-50 | 35-45 |
| 3 | 50-70 | 55-65 |
| 4 | 70-90 | 75-85 |

Figure 6D:
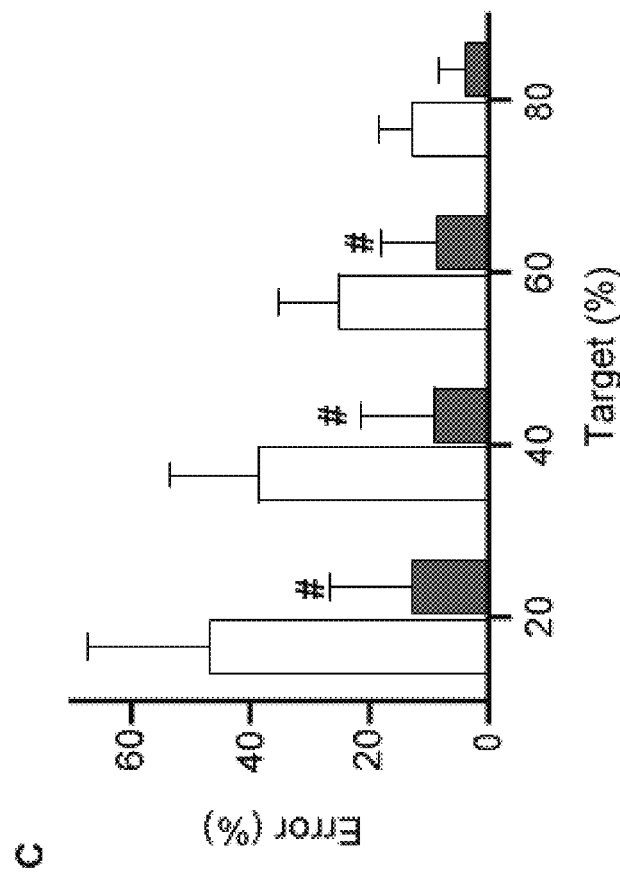
FIG. 6d is a chart showing the effect of stimulation, according to an embodiment of the subject invention, on the time required to achieve target levels of virtual grasp force.

FIG. 6d is a chart showing the effect of stimulation according to certain aspects of the subject invention on the time required to achieve target levels of virtual grasp force. Task durations were significantly longer with STIM (solid filled bars on the right) than NO-STIM (unfilled empty bars on the left), regardless of the target level. Comparisons in this chart used two-way repeated measures ANOVA with Bonferroni multiple pairwise post-hoc comparisons (*$p<0.05$, ˆ$p<0.01$, #$p<0.001$)

FIG. 7 is a ternary graph representation of perceived object profile success rate by category with and without stimulation in accordance with an embodiment of the subject invention. Significant difference between the mean correctness and the chance value calculated by one sample t-test. For Success Rate by Size: $p=7.05E-06$ ($p<0.0001$). For Success Rate by Hardness: $p=0.00431$ ($p<0.005$). For Success Rate by Both Categories: $p=0.00122$ ($p<0.005$). The chart shows success rate (frequency of correct responses from 0 to 1) for each of three values in each of two data series, on a grid of iso-value success rate triangles from 0 to 1 in increments of 0.2 success rate. The inner triangle represents random chance of a correct guess without Stimulation at 0.500 for size, 0.333 for hardness, and 0.167 for both. The outer triangle represents actual results with Stimulation of 0.986 for size, 0.625 for hardness, and 0.625 for both.

Figure 8:
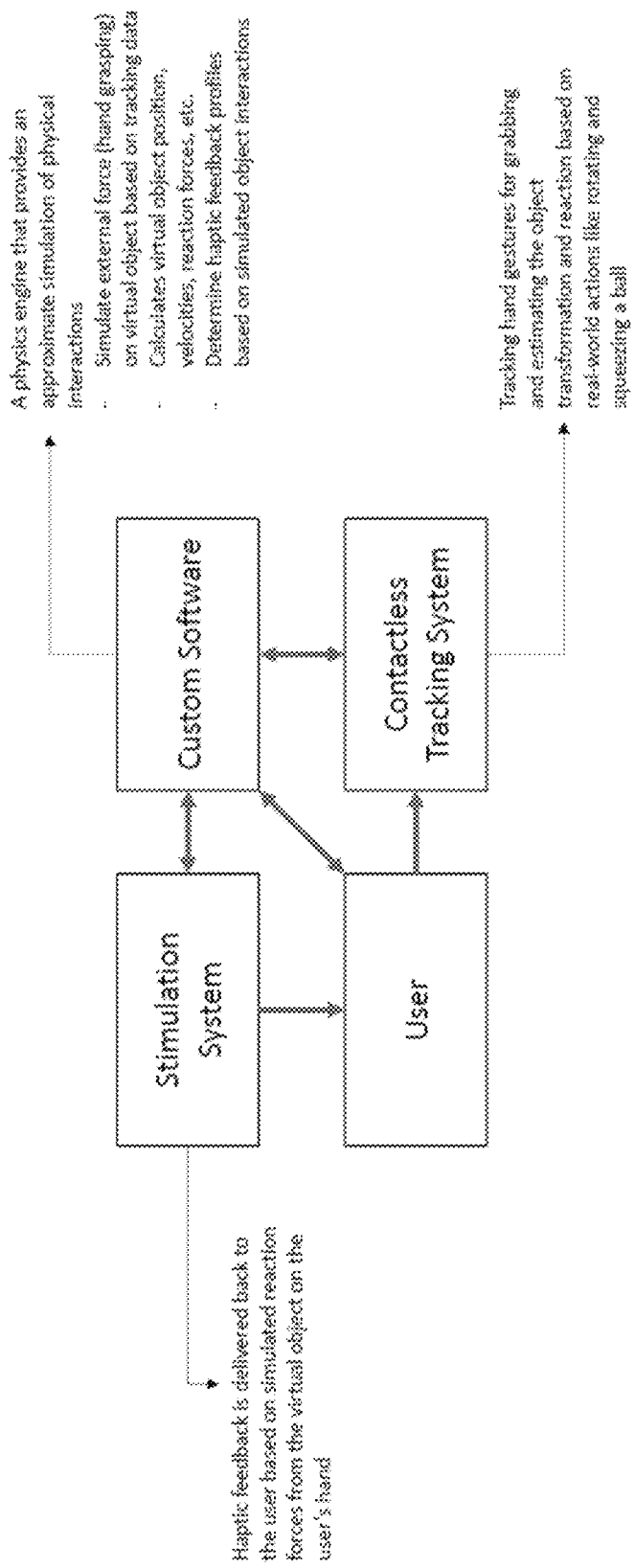
FIG. 8 is a representation of one embodiment of the subject invention showing a user interacting with custom software directly, through a contactless tracking system, and through a stimulation system.

FIG. 8 is a representation of one embodiment of the subject invention showing a user interacting with custom software directly, through a contactless tracking system, and through a stimulation system. Within the stimulation system haptic feedback is delivered back to the user based on simulated reaction forces from the virtual object on the user's hand. Within the custom software a physics engine provides an approximate simulation of physical interactions to (1) simulate external force (hand grasping) on virtual object based on tracking data, (2) calculate virtual object position, velocities, reaction forces, and (3) determine haptic feedback profiles based on simulated object interactions. Within the contactless tracking system tracking of hand gestures is used for grabbing and estimating an object transformation and reaction based on real-world actions including rotating and squeezing a ball.

Figure 9:
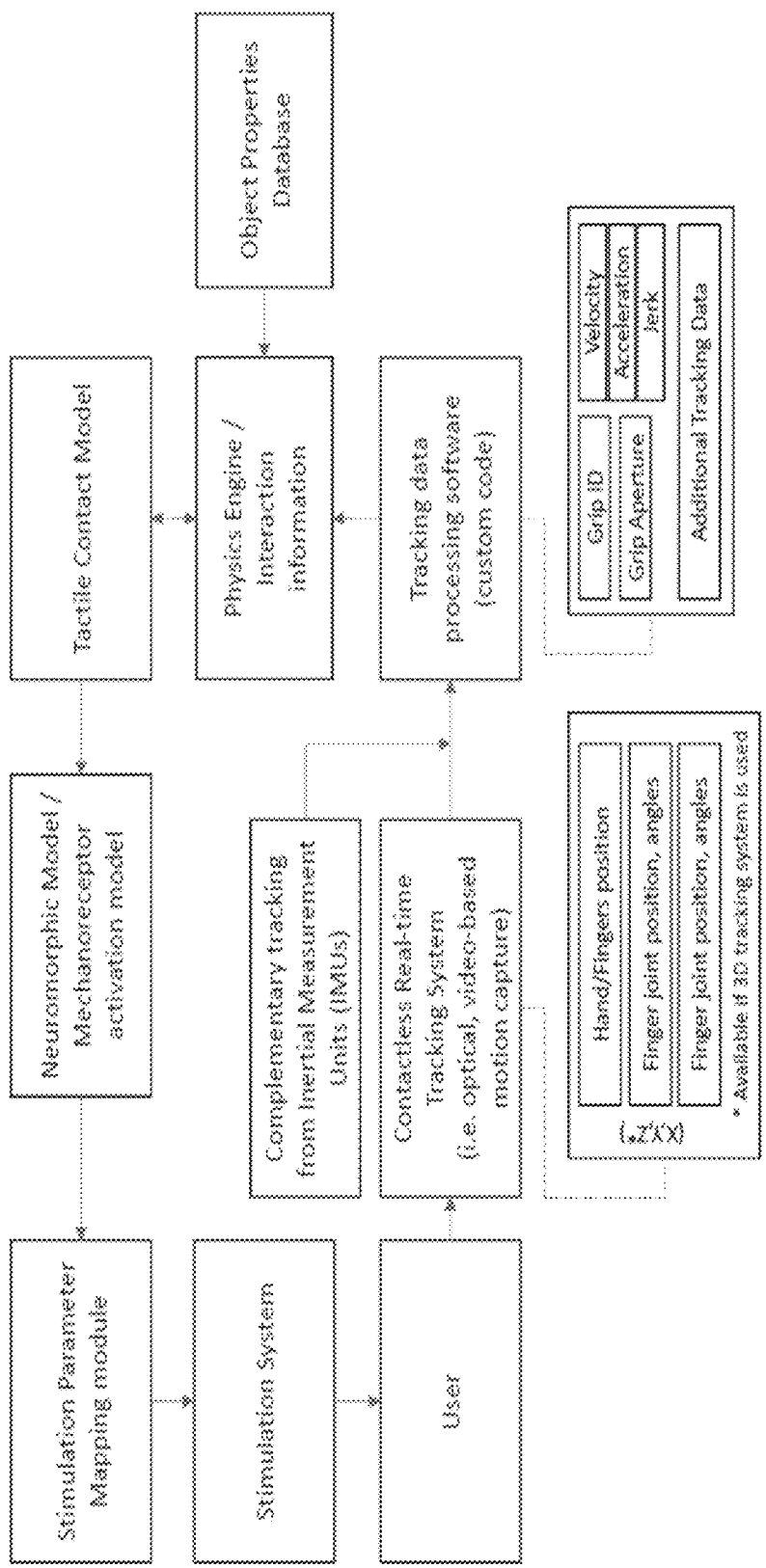
FIG. 9 is a representation of various aspects of one embodiment of the subject invention showing user interactions with custom software through a contactless real-time tracking system and a stimulation system.

FIG. 9 is a representation of various aspects of one embodiment of the subject invention showing user interactions with custom software through a contactless real-time tracking system and a stimulation system. In this embodiment the user receives information, direction, or stimulus from the stimulation system and provides user input via the Contactless Real-time Tracking System (e.g., optical, video-based motion capture) including 2D or 3D representations of hand and finger positions as well as finger joint positions and angles. The contactless real-time tracking system may also include, integrate or interface with complementary tracking from inertial measurement units (IMUs). The contactless real-time tracking system provides input to tracking data processing software (e.g., custom code) which calculates parameters including grip ID, grip aperture, velocity, acceleration, and jerk for input to a physics engine and interaction information module referencing an object properties database to generate and provide input to a tactile contact model which in turn generates and provides input to a neuromorphic model and mechanoreceptor activation model, which in turn generates and provides input to a stimulation parameter mapping module, which then generates and provides input to the stimulation system, which then generates and provides information, direction, or stimulus to the user, thus completing the cycle and closing the system loop.

Figure 10:
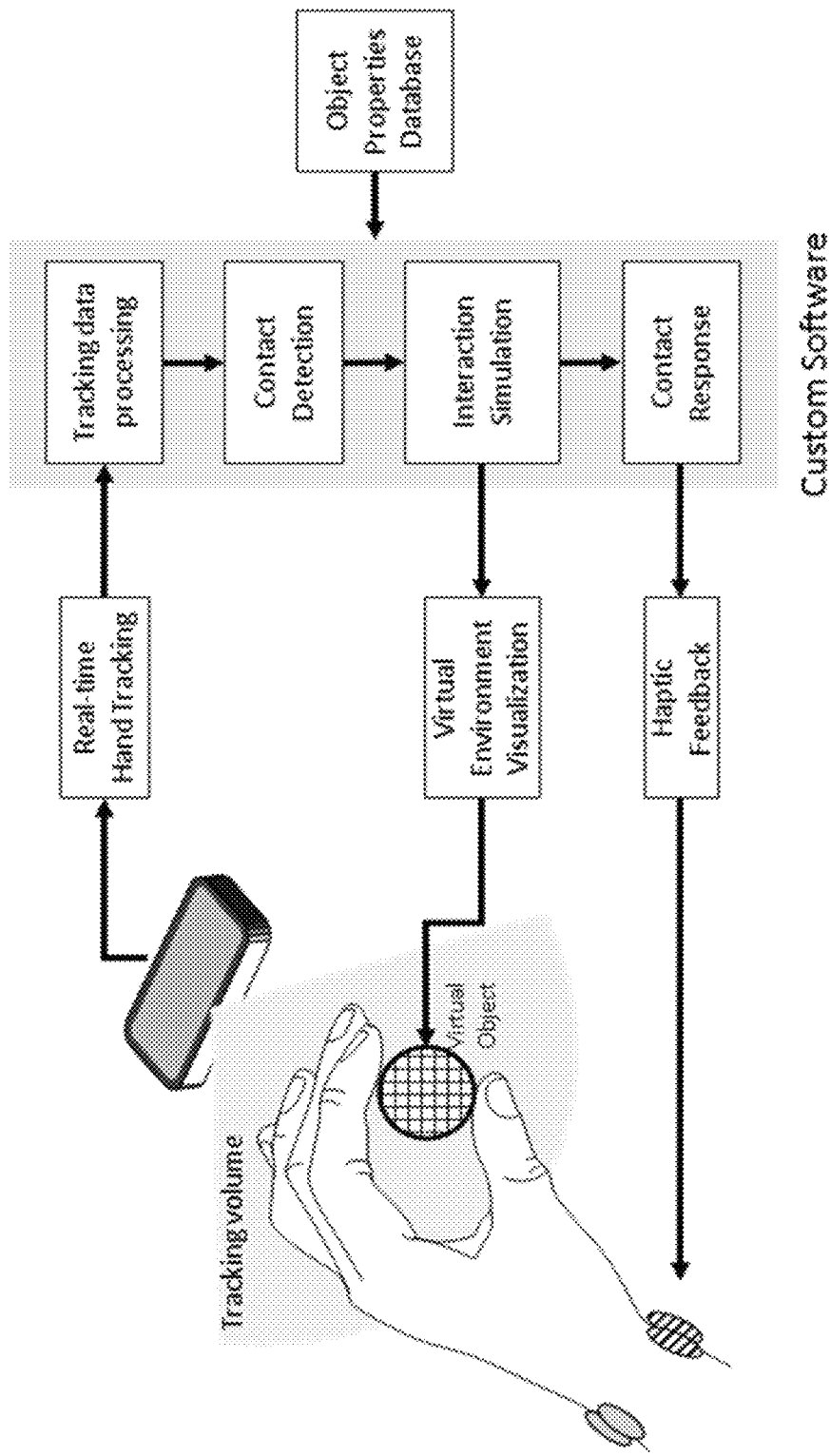
FIG. 10 is a representation of certain elements related to one embodiment of the subject invention showing a user interacting with a virtual object via haptic feedback, virtual environment visualization, and real time hand tracking as controlled by custom software modules referencing an object properties database.

FIG. 10 is a representation of certain elements related to one embodiment of the subject invention showing a user interacting with a virtual object via haptic feedback, virtual environment visualization, and real time hand tracking as controlled by custom software modules referencing an object properties database. In this embodiment, motions of the user's hand within the tracking volume are read by a tracking device into a real-time hand tracking module for input to the custom software and tracking data processing. A tracking data processing module within the custom software may generate and provide input to a contact detection module within the custom processing software. The contact detection module may generate and provide input to an interaction simulation module within the custom software. The interaction simulation module may generate and provide input to a virtual environment visualization module which then generates data and parameters referencing the virtual object in relation to the data captured by the real-time hand tracking module in relation to the user's hand. The virtual environment visualization module may also generate and provide visual information including feedback to the user or to an observer of the user. The interaction stimulation module may also generate and provide input to a contact response module within the custom software. The contact response module may generate and provide input to a haptic feedback module which may then generate and provide haptic feedback to the user.

Potential applications for embodiments of the subject invention include delivering more realistic and intuitive feedback during manipulation and interactions within virtual, augmented, and real environments. These include haptic feedback for gaming, surgical procedure training, physical and neurological rehabilitation and social interactions within virtual worlds without the cumbersome restrictions of traditional haptic hardware.

Embodiments of the subject invention can also be used to deliver haptic feedback for teleoperation of complex surgical robotic devices, as well as remote control of unmanned aerial and terrestrial vehicles designed to minimize risk to civilian and military personnel during unsafe activities from emergency rescue and firefighting missions, to transport and disposal of explosives or dangerous substances.

For individuals with amputation, replacement haptic feedback in accordance with certain embodiments of the subject invention could be implemented in training environments to help improve the functionality of prosthetic limbs, enabling them to classify the physical properties of different objects, and perform fine control of grasp force outputs without the need for visual or auditory feedback.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

MATERIALS AND METHODS

Surface electrical neurostimulation is a non-invasive alternative for providing somatotopically-matched sensory feedback. In this approach, electrical pulses delivered from electrodes on the forearm skin have been shown to activate afferent pathways in the median and ulnar nerves, evoking distally referred sensations. However, traditional methods for surface stimulation are hampered by inadequate electrode and stimulation parameter fitting, poor selectivity, limited percept modulation, and distracting sensations due to localized charges activating tactile afferents in the skin close to the electrodes. These sensations can be hard to ignore, affecting the overall performance of the sensory feedback.

Certain embodiments of the subject invention may use an enhanced surface electrical neurostimulation (eSENS) platform that is able to elicit distally referred tactile percepts while avoiding the local sensations and skin discomfort associated with the large charge densities in traditional methods. In tests involving one embodiment of the subject invention, able-bodied subjects received interleaved current pulses from surface electrodes strategically distributed and applied to the skin around their right wrist, using a Channel-hopping Interleaved Pulse Scheduling (CHIPS) strategy. CHIPS is a multi-channel approach designed to deliver interleaved current pulses from independent stimulation channels, hopping across multiple strategically distributed surface electrodes. By leveraging the combined influence of the interleaved current pulses, each independent channel can be set to stimulate at shorter pulse widths than single-channel stimulation, thus reducing the total charge per pulse delivered by any given electrode, while maintaining net charge delivery to the target nerve at functional levels. In other words, the stimulation is sub-threshold for cutaneous activation near each electrode, but supra-threshold at the level of the nerve due to the spatiotemporal summation of the interleaved pulses (see also Geng et al., Impacts of selected stimulation patterns on the perception threshold in electrocutaneous stimulation. J Neuroeng Rehabil, 8, 9, 2011; and Brunton et al., Temporal Modulation of the Response of Sensory Fibers to Paired-Pulse Stimulation. IEEE Transactions on Neural Systems and Rehabilitation Engineering, 27, 1676-1683, 2019; both of which are hereby incorporated by reference herein in their entireties).

CHIPS leverages the combined influence of sub-threshold pulses to deliver functional stimulation to the nerve, evoking distally referred sensations more efficiently and comfortably than traditional methods. This provided evidence that the novel CHIPS strategy addresses some of the issues hindering surface stimulation from being adopted as a viable option for intuitive sensory feedback. A charge-rate modulation in accordance with certain embodiments of the subject invention was evaluated during psychophysical studies and incorporated into the tests described below. Implementation of this encoding strategy demonstrated enhancement of the range and gradation of evoked percept intensities with the eSENS platform. This strategy could be used to provide relevant sensory information during functional tasks. The relationship between the stimulation parameters used for this encoding strategy allowed for the implementation of "user-in-the-loop" (UiTL) calibration routines to streamline the stimulation parameter fitting process.

One goal of the examples described here was to investigate the ability of certain embodiments of the subject invention including the eSENS platform to convey graded (e.g., a range of different intensity levels) and discriminable (e.g., the subject is able to discern between the different intensity levels) levels of sensory information for intuitive haptic feedback during functional tasks. To this end, two different functional task paradigms were developed to assess the functional benefits afforded by the enhanced haptic feedback on the subject's ability to (1) grasp and classify virtual objects with different size and hardness characteristics and (2) perform graded closed-loop control of virtual grasp force outputs. It was hypothesized that functional classification of different virtual grasping force profiles delivered by certain embodiments of the subject invention including the eSENS platform would be better than chance. This was tested by quantifying the rate at which able-bodied subjects successfully classified different virtual objects according to their perceived size and hardness. It was also hypothesized that graded control of virtual grasp force outputs would be significantly better in the presence of grasp force feedback from the neurostimulator in accordance with certain embodiments of the subject invention. This was tested by quantifying the ability of able-bodied subjects to accurately reach different target force levels by controlling the virtual force outputs with a proportional control joystick. Results from these functional studies provide compelling evidence that the tactile percepts delivered by the eSENS platform with the implementation of the CHIPS strategy and charge-rate encoding in accordance with certain embodiments of the subject invention, could be readily utilized by able-bodied subjects to complete functional tasks without the need for visual feedback. The task-related information provided by this sensory feedback approach could also be used to close the loop between individuals with upper limb amputations and their prosthesis.

The examples were intended to investigate the ability of embodiments of the subject invention including the eSENS platform to convey task-related sensory feedback to able-bodied subjects. The potential functional benefits afforded by the supplementary feedback were assessed in a series of grasp profile classification and graded force control studies.

Written informed consent was obtained from four right-handed adult subjects (2 males, 2 females, mean age ±SD: 27±4.7) in compliance with the Institutional Review Board of Florida International University which approved the study protocol. All prospective subjects were screened prior to the study to determine eligibility. Subjects were able-bodied, with no sensory disorders or any self-reported condition listed as a contraindication for transcutaneous electrical stimulation (pregnancy, epilepsy, lymphedema, or cardiac pacemaker) (Rennie, 2010).

In accordance with certain embodiments of the subject invention median nerve stimulation was delivered transcutaneously by four self-adhesive hydrogel electrodes (Rhythmlink International LLC, Columbia, S.C.) placed at the subject's right wrist. A multi-channel programmable, optically isolated benchtop bio-stimulator (TDT IZ2-16H, Tucker-Davis Technologies (TDT), Alachua Fla. USA) was used to deliver charge-balanced, current-controlled biphasic rectangular pulses following the CHIPS strategy. The stimulator was controlled by a TDT Synapse stimulation control environment with a custom MATLAB (v2019b, MathWorks Inc, Natick, Mass.) program. Additional information regarding the surface electrical neurostimulation procedure can be found in Pena (Andres Pena, Enhanced Surface Electrical Neurostimulation (eSENS): A Non-Invasive Platform for Peripheral Neuromodulation; Doctoral Dissertation, 2020; which is hereby incorporated by reference herein in its entirety), particularly in Chapter 3 thereof.

In accordance with certain embodiments of the subject invention subjects were seated on a chair with both arms on a table in front of them (see FIG. 1). Their right forearm was thoroughly cleaned with a wet wipe and fitted with a distributed set of surface electrodes at their right wrist. The right forearm was placed on a support pad on the table with their hand's palmar surface parallel to the vertical plane. A computer screen was located in front of the subject at eye level. The screen displayed instructions, visual cues of the target levels and, in trials that used visual feedback, a visual indicator of performance. A custom 3-button keyboard and a control knob were placed on the table during the stimulation parameter fitting procedure. As shown in FIG. 1, subjects were seated on a chair and fitted with the surface stimulation platform using the CHIPS strategy. A screen in front of the subject displayed visual cues and feedback signals. (A) A custom 3-button keyboard and a control knob were placed on the table during the stimulation parameter fitting procedure only. (B) During the functional studies, a hand aperture tracking device (LEAP Motion Controller) was placed on the right side of the table, while a custom-made proportional control joystick was placed on the left side. The keyboard was used to provide percept responses, while the knob was used to adjust various stimulation parameters at different stages of the stimulation fitting process. The knob was set to control stimulation parameter values within safe levels. The keyboard and knob were removed upon completion of the stimulation fitting process.

In accordance with certain embodiments of the subject invention, during the functional studies, a Leap Motion Controller (Ultraleap, Mountain View, Calif. USA) was placed on the right side of the table, while a custom made proportional control joystick was placed on the left side (see FIG. 1). The Leap Motion controller is an optical hand-tracking module that was used to capture the movements of the subject's hand during the virtual object classification studies. The joystick was used by the subject to reach different virtual grasp force target levels during the graded force control studies. Subjects were encouraged to drink water before and during the experiment to increase skin hydration. They were instructed to concentrate throughout the experiment but were encouraged to stretch and move their hand during periodic breaks to prevent discomfort. They were also asked about their comfort levels, or if additional breaks were needed after each task.

EXAMPLE 1

Stimulation Parameter Fitting

Pulse Amplitude (PA) thresholds were obtained from all subjects under five different Pulse Width (PW) values (300 μs to 700 μs, at 100 μs intervals). The order of the pulse widths was randomized across all subjects. During the PA threshold determination procedure, subjects triggered the delivery of a pulse train with constant 5 Hz Pulse Frequency (PF) by pressing the "Go" button on a keyboard, and then used a custom control knob to adjust the PA (from 0 μA to 3000 μA) to find the lowest possible level that evoked a percept. These responses were used to derive the strength-duration (SD) profile for each subject. The stimulation pulse amplitude used throughout this study was set to 50% above the percept threshold (1.5×PAth) at a PW of 500 μs.

Conveying a wide range of graded percept intensities was achieved by adjusting both PW and PF simultaneously, along their operating ranges (charge-rate encoding). The lower and upper limits of these operating ranges were also determined through a similar subject-controlled calibration routine.

First, stimulation was delivered at a fixed PF of 100 Hz while instructing the subjects to use the knob to explore a wide range of PW (from 100 μs to 800 μs) to find the lowest possible level that evoked a reliable percept, and the highest possible level that did not cause discomfort. Lastly, the stimulation PW was set to the midpoint of the recently obtained PW range, and the subjects were again instructed to use the knob to explore a wide range of PF (from 30 Hz to 300 Hz) to find the lowest possible frequency that was not perceived as pulsating (fusion), and the level at which the perceived stimulation intensity did not change (saturation). Once the range limits were obtained, the stimulation fitting was complete. A questionnaire was used to interrogate the perceived modality, quality and location of the evoked sensations along the fitted parameter range. Additional information regarding the stimulation parameter fitting procedure can be found in Pena (supra.), particularly in Chapter 4 thereof.

EXAMPLE 2

Virtual Object Classification Task

Virtual object classification tasks were completed to determine whether subjects were able to distinguish between different percept intensity profiles designed to emulate grasping forces during manipulation of various objects of different size and hardness. Six unique virtual profiles were created for this study (Table 3). These included all possible combinations of two size levels (small, large) and three hardness levels (soft, medium, hard).

During these tasks, the subject's right hand and fingers were tracked in real time using a Leap Motion tracking module that was placed in front of them. A custom MATLAB algorithm was used to parse the hand tracking data from the Leap Motion software (Orion 3.2.1 SDK) and calculate the subject's hand aperture distance (linear distance between the thumb pad and the average horizontal position of the index, middle and ring finger pads; FIG. 2, Panel A). The hand aperture data was used to determine whether the subjects were making contact with a virtual object of a preset size and hardness. If the hand aperture was equal or less than the virtual object's uncompressed size (FIG. 2, Panel B), the algorithm estimated the amount of object compression and resulting grasping force. The full compressive range of the virtual object was linearly mapped to the full range of percept intensities. Hard objects were assigned a small compressive range to allow the stimulation to reduce the chances of a sharp increase in stimulation intensity. A compressive range for a Small-Medium object can be 40 mm–28 mm=12 mm range, while a compressive range of a Large-Hard object can be 80 mm–78 mm=2 mm range.

TABLE 6

Virtual object profiles used during the classification tasks

| Virtual | Uncompressed | Compressed |
| --- | --- | --- |
| Small-Soft | 40 | 12 |
| Small-Medium | 40 | 28 |
| Small-Hard | 40 | 38 |
| Large-Soft | 80 | 24 |
| Large-Medium | 80 | 56 |
| Large-Hard | 80 | 78 |

Each virtual grasp trial began with the subject opening their right hand to an aperture of >10 cm and placing it in front of the sensor. Once the hand was detected in place, they were asked to slowly close the hand to "squeeze" the virtual object until they began feeling the stimulation. Subjects were encouraged to open and close their hand as many times as needed to determine the object size and hardness, within a period of 60 seconds. Subjects were instructed to "squeeze" the virtual object and pay attention to how the perceived stimulation intensity was ramped up. For instance, squeezing a hard object would ramp up the perceived grasp force much faster than a more compressible, softer object. Subjects were encouraged to open and close their hand as many times as needed to determine the object size and hardness, within a period of 60 seconds. Subjects were instructed to report the perceived size and hardness of the virtual object. For example, if subjects perceived they were grasping a large object that felt soft, they would say "large and soft". Subjects were blindfolded to prevent any visual feedback of hand aperture.

The experiment started with a practice block in which all unique profiles were presented and identified to the subject twice. Each subject then completed 2 experimental blocks of 18 non-repeating, randomized virtual grasp trials (6 repetitions per profile), resulting in a total of 36 double-blinded presentations. Subjects were allowed to take as many breaks as they needed. For each trial, the subject's response was compared to the virtual object profile used. The frequency of correct responses (success rate) was used as the performance variable.

One-sample t-tests were performed to determine if the success rate was significantly greater than chance. During virtual object classification, the chance of correctly identifying the object size or hardness alone was 50% and 33.3% respectively, while the chance of correctly identifying size and hardness together was 16.7%.

EXAMPLE 3

Graded Grasp Force Control Task

Tests for graded control of virtual grasp force outputs were conducted to evaluate the subject's ability to utilize the feedback delivered by the eSENS platform to control virtual grasp force outputs in a graded manner in the absence of visual feedback. Subjects used a proportional control joystick (FIG. 4A) with their left hand to adjust the level of grasp force applied by an invisible virtual hand. Briefly, the position of the joystick (degree of deflection) was proportionally mapped to the rate of change of virtual grasp force. A randomized scaling factor was added to the proportional control map, resulting in subtle changes to the rate of change of force in each trial. The full range of grasp force outputs of the virtual hand was linearly mapped to the full range of intensities perceived by the subject on their right hand.

Subjects were presented a target value of the grasp force output of the virtual hand on a computer display (FIG. 4B) and asked to match that target by adjusting the level of grasp force with the proportional control joystick; subjects verbally indicated acquisition of the target by saying "there". The display consisted of a white thermometer bar scaled to the full virtual force range. A moving bar provided absolute feedback of the grasp force level. The moving bar was not visible during the "no visual feedback" condition. A target zone box (target level±7%) was used to show a target value of 20, 40, 60, or 80%.

Each trial consisted of a series of target presentations over a range of 0 to 100% of the maximum percept intensity range. The sequence of target values in a given trial was drawn from a set of pre-specified sequences that were varied across trials. Target sequences alternated between 0% and a non-zero level (20, 40, 60, or 80%). An experiment block consisted of 33 trials in which the target alternated between different levels presented randomly. A single experimental sequence started with a block of practice trials to familiarize the subject with the information provided in the experimental display while receiving visual and stimulation feedback together (STIM+VISION). The practice block was followed by two blocks of control trials for each condition without visual feedback: No Stimulation feedback (NO-STIM) and Stimulation feedback only (STIM) in which only the target zone box was shown. Periodic breaks were interspersed among the experiment blocks.

Data from these trials included the target level and continuous measurements of virtual grasp force levels. The value of the grasp force output achieved was determined as the average of the measured values obtained over the last 250 ms for each target (match level). Match error was set to zero when the match level was inside the target zone (target level±7%); otherwise, match error was calculated as the distance from the match level to the nearest target zone border. The time it took to reach each target level was also recorded. These data sets provided quantitative measures of the quality of control actions afforded by the feedback from the eSENS platform.

To assess the impact of sensory feedback on the ability of the subject to control the virtual force outputs in a graded manner, a two-way repeated measures ANOVA with Bonferroni multiple pairwise post-hoc comparisons was used to assess the effects of stimulation and target value on performance ($p<0.05$). Only data from 20, 40, 60, and 80% target level trials were considered in this analysis.

Four able-bodied subjects received transcutaneous stimulation from a neurostimulation platform enhanced by the novel CHIPS strategy in accordance with an embodiment of the subject invention. This approach evoked comfortable distally referred sensations of tingle, pressure and vibration in the general area innervated by the sensory fibers in the median nerve (palmar surface, index, middle, and part of the ring finger). All subjects selected the appropriate stimulation amplitude levels, and operating ranges for Q and PF with a subject-controlled calibration routine. Percept intensity was encoded by modulating charge-rate (QR) over an average range spanning from $1.17\pm1.43$ μA to $139.62.97\pm24.10$ μA. All surface electrodes had impedance values (mean±SD) of at $27.34\pm1.43$ kΩ, which remained stable for all subjects throughout the study. No uncomfortable or local sensations, and no side effects like irritation or redness of the skin were observed in any of the able-bodied subjects.

EXAMPLE 4

Subjects Successfully Classified Virtual Objects by Their Size and Hardness with Feedback from eSENS Subjects were able to integrate percept intensity information delivered by the neurostimulator in accordance with an embodiment of the subject invention as they grasped virtual objects (FIG. 5A) in front of them to successfully determine their size and hardness, (FIG. 5B). During an experimental session, each of six virtual object profiles was presented six times, for 36 double-blinded presentations. Subjects were able to differentiate between large and small objects much better than chance, with an average success rate (mean±SD) of $98.61\pm2.77\%$, $p<0.0001$. Subjects successfully classified virtual objects by their hardness with success rates significantly greater than chance for large objects ($70.83\pm23.70\%$, $p<0.001$) and small objects ($54.17\pm26.71\%$, $p=0.019$). All subjects successfully classified both object size and hardness combined, with success rates significantly greater than chance ($62.5\pm17.84\%$, $p<0.005$).

EXAMPLE 5

Subjects Demonstrated Graded Control of Virtual Grasp Force with Feedback from eSENS Subjects were able to guide their control actions in a graded manner to reach virtual grasp force target levels with sensory feedback enabled (i.e. the STIM condition) in the absence of visual feedback (FIGS. 6a, 6b, 6c, 6d). Error was set to zero when the match level was inside the target zone (±7%); otherwise, error was calculated as the distance from the match level to the nearest target zone border. The match level (mean±SD) was significantly lower with STIM (filled bars) than NO-STIM (empty bars) for target levels of 20%, 40% and 60% ($F_{1,23}=29.59$, $p<0.0001$, $n=24$ per target). Match levels were significantly different between adjacent target levels 40% and 60% with STIM (p=0.0029) and between adjacent target levels 20% and 40% with NO-STIM (p=0.0271). Shaded boxes indicate the target zone for each target level (FIG. 21B). The error (mean±SD) was significantly lower with STIM than NO-STIM (8.66±3.77% and 30.84±15.03%, respectively; $F_{1,23}$=41.21, p<0.0001, n=24 per target). More specifically, the error was lower with STIM for target levels of 20%, 40% and 60% (p<0.0001; FIG. 6C). In average, subjects took significantly longer to attempt each target (FIG. 6D) with STIM (5.63±0.2 s) than with NO-STIM (2.26±0.5 s), regardless of the target level ($F_{1,23}$=89.18, p<0.0001, n=24 per target).

The examples sought to determine if able-bodied subjects could utilize feedback delivered by an enhanced surface electrical neurostimulation (eSENS) platform in accordance with embodiments of the subject invention to successfully classify the perceived physical characteristics of virtual objects, and execute graded control of virtual grasp force outputs. Able-bodied subjects received transcutaneous stimulation from surface electrodes at the wrist. The stimulation performance was enhanced by the novel CHIPS strategy, and charge-rate intensity encoding. This resulted in comfortable distally referred sensations with a wide range of graded intensities, in the areas of the hand innervated by the median nerve afferents. The size and hardness of different virtual objects were encoded by changes in the intensity of the artificial percept during a grasping action such that the object's full compressive range contained the full range of percept intensities. In a similar way, percept intensities were mapped to the full range of grasp forces from the virtual hand during graded control tasks. Subjects successfully recognized virtual objects by their size and hardness combined about 67% of the time, which was much better than chance (17%). Subjects were also able to use the feedback information to reach different target levels without visual feedback with significantly lower errors than when the stimulation was turned off.

The information delivered by the neurostimulator according to certain embodiments of the subject invention is intuitive and not distracting to reduce cognitive loading. It provides relevant feedback enabling the user to make control decisions and reduce error, allowing for closed-loop control of their own actions or the actions of an external device such as a prosthetic limb, thus affording functional advantages to the user. While the virtual object classification task in this example did not explicitly require the subject to perform graded control actions, the grasping action they performed while exploring the object's characteristics was guided by the feedback they received from the stimulator. At first, subjects were instructed to squeeze the object slowly to appreciate its perceived compliance and size. When exhausting the full compressive range of a soft or medium hardness object, subjects typically reversed course and began to open the hand (FIG. 5A), suggesting that they perceived the object as fully compressed. Subjects were asked to squeeze the object multiple times without specifying a hand closing speed. Without wishing to be bound by theory, the inventors hypothesize that hand closing speed may play a role in classification performance and it is contemplated within the scope of certain embodiments of the subject invention to calibrate system response and neurostimulation feedback by hand closing speed. In addition, subjects often reported perceiving the virtual object as something between a sphere and a cube that conformed to their hand. This could be because the stimulation only delivered information about the size and hardness based solely on hand aperture tracking. Therefore, no changes in object characteristics were perceived after wrist rotation or changing hand positions. Without wishing to be bound by theory, the inventors hypothesize that in accordance with certain embodiments of the subject invention tracking the aperture of individual fingers as well as the hand position may allow for more complex virtual object manipulation information to be delivered by the neurostimulator, and it is contemplated that in accordance with certain embodiments of the subject invention tracking data may include the position, distance, or aperture of one or more individual fingers as well as one or more of the position, angle, orientation, or pose of one or more fingers, finger joints, hands, wrists, or arms to then allow for more complex virtual object manipulation or user object interaction information. Finally, most subjects reported feeling confused at first by the lack of object resistance, especially for large-hard and large-medium objects. However, all of them reported that this feeling subsided during the classification tasks, suggesting that subjects were able to internalize the feedback as compression force. Without wishing to be bound by theory, the inventors hypothesize that certain embodiments of the subject invention may benefit from a training or normalization period where a subject learns to better understand and respond to the information provided by the neurostimulator, and it is contemplated that in accordance with certain embodiments of the subject invention methods may include a training or normalization period where a subject learns to better understand and respond to the information provided by the neurostimulator.

Performance results from the graded control tasks suggest that feedback from the eSENS platform according to certain embodiments of the subject invention affords functional advantages to the subjects by providing relevant information to inform their control actions. As seen in FIG. 5A, subjects used sensory feedback to correct their error when moving past the target. Because of this corrective action, subjects generally took significantly longer to complete control tasks in the presence of stimulation feedback, regardless of the target level. In contrast, absence of stimulation or visual feedback also meant that subjects did not receive error cues, thus reducing or preventing corrective actions, which in turn reduced task durations while simultaneously increasing task error.

User object interaction information can include characteristics of the user's interaction with a virtual object, including but not limited to grip type, grasp force, hand position, and hand closing velocity. A tactile contact model can include a mechanical model of the interaction between an object with specific mechanical properties and the human skin in hand and fingers. A neuromorphic mechanoreceptor activation model can include a biomimetic model of the sensory receptor/axon firing patterns that would be expected when an object is manipulated in the same way the virtual object is manipulated. An enhanced neurostimulation response signal can include neurostimulation using parameters for more natural neural patterning (i.e., time-variant parameters for evoking more naturalistic sensations than the traditional, synchronous/time-invariant stimulation).

A minimum pulse amplitude perceptible to the user can be the percept threshold, and it can vary across people and stimulation approach used; for surface stimulation around the wrist, on average this value can be between 0.5 mA to 3 mA depending on age, gender, skin conditions, and other factors. A maximum pulse amplitude creating discomfort in the user can be the percept threshold, and it can vary across people and stimulation approach used; for surface stimulation around the wrist, on average this value can be between 1.5 mA to 6 mA depending on age, gender, skin conditions, and other factors. The maximum amplitude is not limited to this range; this is for exemplary purposes only. A minimum pulse width detectable to the user and a maximum pulse width creating discomfort in the user can depend on the pulse amplitude used. The pulse width-pulse amplitude relationship for detection threshold can be seen in a strength-duration curve. A minimum fusion pulse frequency perceptible to the user can depend on the user; for a specific application using CHIPS, on average this can be for example a fusion frequency of from 50 Hz to 70 Hz. A maximum saturation pulse frequency perceptible to the user can depend on the user; for a specific application using CHIPS, on average this can be for example a fusion frequency in a range of from 200 Hz to 300 Hz.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for providing enhanced surface electrical neurostimulation and haptic feedback to a user within a simulation environment, the system comprising:
    a neurostimulation subsystem,
    a contactless real time tracking subsystem,
    an object properties database,
    a processor; and
    a machine-readable medium in operable communication with the processor, the neurostimulation subsystem, the contactless real time tracking subsystem, and the object properties database, the machine-readable medium having instructions stored thereon that, when executed by the processor, perform the following steps:
        collecting, from at least one of the neurostimulation subsystem, the contactless real time tracking subsystem, and the object properties database, data comprising user input data, tracking data, and object properties data;
        processing the object properties data and the tracking data to create user object interaction information, a tactile contact model, and a neuromorphic mechanoreceptor activation model;
        processing the user input data and the neuromorphic mechanoreceptor activation model to create an enhanced neurostimulation response signal; and
        delivering the enhanced neurostimulation response signal to the neurostimulation subsystem, thereby providing the enhanced surface electrical neurostimulation and haptic feedback,
    the neurostimulation response signal comprising one or more stimulation parameters derived from the user input data to fit the one or more stimulation parameters to an individual user based on user feedback, and
    the one or more stimulation parameters comprising at least one of a pulse amplitude (PA) of less than 3000 microamps (µA), a pulse width (PW) of less than 800 microseconds (µs), and a pulse frequency (PF) of less than 300 Hz.

2. The system according to claim 1, the contactless real time tracking subsystem configured to track a hand or fingers of the user, and the neurostimulation subsystem comprising 2 pairs of self-adhesive hydrogel electrodes placed on a wrist of the user over a median nerve of the user and configured to evoke distally referred tactile percepts in the user when powered in accordance with the enhanced neurostimulation response signal.

3. The system according to claim 2, the tracking data comprising a non-contact motion capture output comprising at least one of a one-dimensional (1D) representation, a two-dimensional (2D) representation, and a three-dimensional (3D) representation of at least one of the following: hand position; finger position; finger joint position; finger joint angle; location of any two fingers or visible surfaces of the hand of the user; and distance between any two fingers or visible surfaces of the hand of the user.

4. The system according to claim 3, the step of processing the object properties data and the tracking data to create user object interaction information, a tactile contact model, and a neuromorphic mechanoreceptor activation model further comprising calculating one or more parameters selected from the group consisting of grip ID, grip aperture, velocity, acceleration, and jerk.

5. The system according to claim 4, the object properties data comprising at least one of object size data and object hardness data for one or more objects, each object of the one or more objects being a real object or a virtual object.

6. The system of claim 1, the neurostimulation response signal comprising one or more current controlled, biphasic, anodic pulse sequences, each sequence having at least one stimulation parameter selected from the group consisting of a PA, a PW, and a PF,
    the PA being greater than a minimum amplitude of 30 µA,
    the PA being less than a maximum amplitude of 3000 µA,
    the PW being greater than a minimum width of 100 µs,
    the PW being less than a maximum width of 800 µs,
    the PF being greater than a fusion frequency of 30 Hz, and
    the PF being less than a saturation frequency of 300 Hz.

7. The system of claim 6, the neurostimulation response signal comprising interleaved sub-threshold current pulses using a channel hopping interleaved pulse scheduling strategy and a bio-inspired charge rate encoding strategy configured to deliver functional stimulation to a proximal nerve and evoke one or more distally referred tactile percepts in the user at a charge density of less than 30 microcoulombs per square centimeter ($\mu C/cm^2$).

8. A method for providing enhanced surface electrical neurostimulation and haptic feedback to a user within a simulation environment, the method comprising:
    providing a neurostimulation subsystem in operable communication with the user;
    providing a contactless real time tracking subsystem in operable communication with the user;
    providing an object properties database;
    collecting data from at least one of the neurostimulation subsystem, the contactless real time tracking subsystem, and the object properties database, the data comprising user input data, tracking data, and object properties data, and the collecting being performed by a processor in operable communication with the neurostimulation subsystem, the contactless real time tracking subsystem, and the object properties database;
    processing, by the processor, the object properties data and the tracking data to create user object interaction information, a tactile contact model, and a neuromorphic mechanoreceptor activation model;

processing, by the processor, the user input data and the neuromorphic mechanoreceptor activation model to create an enhanced neurostimulation response signal; and providing, by the processor, the enhanced neurostimulation response signal to the neurostimulation subsystem, thereby providing the enhanced surface electrical neurostimulation and haptic feedback, the tracking data comprising a non-contact motion capture output comprising at least one of a one-dimensional (1D) representation, a two-dimensional (2D) representation, and a three-dimensional (3D) representation of at least one of the following: hand position; finger position; finger joint position; finger joint angle; and locations of, and distance between, any two fingers or visible surfaces of a hand of the user, the step of processing, by the processor, the object properties data and the tracking data to create user object interaction information, a tactile contact model, and a neuromorphic mechanoreceptor activation model further comprising calculating one ore more parameters selected from the group consisting of grip ID, grip aperture, velocity, acceleration, and jerk, the object properties data comprising at least one of object size data and object hardness data for one or more objects, each object of the one or more objects being a real object or a virtual object, and the one or more stimulation parameters comprising a pulse amplitude (PA) of less than 3000 microamps ($\mu A$), a pulse width (PW) of less than 800 microseconds ($\mu s$), and a pulse frequency (PF) of less than 300 Hz.

9. The method of claim 8, the neurostimulation response signal comprising one or more current controlled, biphasic, anodic pulse sequences, each sequence having at least one stimulation parameter selected from the group consisting of a PA, a PW, and a PF, the PA being greater than a minimum amplitude of 30 $\mu A$,
the PA being less than a maximum amplitude of 3000 $\mu A$,
the PW being greater than a minimum width of 100 $\mu s$,
the PW being less than a maximum width of 800 $\mu s$,
the PF being greater than a fusion frequency of 30 Hz, and
the PF being less than a saturation frequency of 300 Hz.

10. The method of claim 9, the neurostimulation response signal comprising interleaved sub-threshold current pulses using a channel hopping interleaved pulse scheduling strategy and a bio-inspired charge rate encoding strategy configured to deliver functional stimulation to a proximal nerve and evoke one or more distally referred tactile percepts in the user at a charge density of less than 30 microcoulombs per square centimeter ($\mu C/cm^2$).

11. A system for providing enhanced surface electrical neurostimulation and haptic feedback to a user within a simulation environment, the system comprising:
a neurostimulation subsystem,
a contactless real time tracking subsystem,
an object properties database,
a processor; and
a machine-readable medium in operable communication with the processor, the neurostimulation subsystem, the contactless real time tracking subsystem, and the object properties database, the machine-readable medium having instructions stored thereon that, when executed by the processor, perform the following steps:
collecting, from at least one of the neurostimulation subsystem, the contactless real time tracking subsystem, and the object properties database, data comprising user input data, tracking data, and object properties data;

processing the object properties data and the tracking data to create user object interaction information, a tactile contact model, and a neuromorphic mechanoreceptor activation model;

processing the user input data and the neuromorphic mechanoreceptor activation model to create an enhanced neurostimulation response signal;

delivering the enhanced neurostimulation response signal to the neurostimulation subsystem, thereby providing the enhanced surface electrical neurostimulation and haptic feedback, the contactless real time tracking subsystem configured to track a hand or fingers of the user, the neurostimulation subsystem comprising 2 pairs of self-adhesive hydrogel electrodes placed on a wrist of the user over a median nerve of the user and configured to evoke distally referred tactile percepts in the user when powered in accordance with the enhanced neurostimulation response signal, the tracking data comprising a non-contact motion capture output comprising at least one of a one-dimensional (1D) representation, a two-dimensional (2D) representation, and a three-dimensional (3D) representation of at least one of the following: hand position; finger position; finger joint position; finger joint angle; location of any two fingers or visible surfaces of the hand of the user; and distance between any two fingers or visible surfaces of the hand of the user, the step of processing the object properties data and the tracking data to create user object interaction information, a tactile contact model, and a neuromorphic mechanoreceptor activation model further comprising calculating one or more parameters selected from the group consisting of grip ID, grip aperture, velocity, acceleration, and jerk, the object properties data comprising at least one of object size data and object hardness data for one or more objects, each object of the one or more objects being a real object or a virtual object, the neurostimulation response signal comprising one or more stimulation parameters derived from the user input data to fit the one ore more stimulation parameters to an individual user based on user feedback, the neurostimulation response signal comprising one or more current controlled, biphasic, anodic pulse sequences, each sequence having at least one stimulation parameter selected from the group consisting of a pulse amplitude (PA), a pulse width (PW), and a pulse frequency (PF), the PA being greater than a minimum amplitude of 30 $\mu A$,
the PA being less than a maximum amplitude of 3000 $\mu A$,
the PW being greater than a minimum width of 100 $\mu s$,
the PW being less than a maximum width of 800 $\mu s$,
the PF being greater than a fusion frequency of 30 Hz, and
the PF being less than a saturation frequency of 300 Hz, and the neurostimulation response signal comprising interleaved sub-threshold current pulses using a channel hopping interleaved pulse scheduling strategy and a bio-inspired charge rate encoding strategy configured to deliver functional stimulation to a proximal nerve and evoke one or more distally referred tactile percepts in the user at a charge density of less than 30 microcoulombs per square centimeter (μC/cm$^2$).

\* \* \* \* \*